United States Patent
Li

(10) Patent No.: US 7,742,163 B2
(45) Date of Patent: Jun. 22, 2010

(54) FIELD REPLACEABLE UNITS (FRUS) OPTIMIZED FOR INTEGRATED METROLOGY (IM)

(75) Inventor: Shifang Li, Pleasanton, CA (US)

(73) Assignee: Tokyo Electron Limited, Tokyo (JP)

( * ) Notice: Subject to any disclaimer, the term of this patent is extended or adjusted under 35 U.S.C. 154(b) by 191 days.

(21) Appl. No.: 12/169,285

(22) Filed: Jul. 8, 2008

(65) Prior Publication Data

US 2010/0007875 A1   Jan. 14, 2010

(51) Int. Cl.
*G01N 21/00* (2006.01)
(52) U.S. Cl. .................................... 356/237.5
(58) Field of Classification Search ........................ None
See application file for complete search history.

(56) References Cited

U.S. PATENT DOCUMENTS

| | | | |
|---|---|---|---|
| 6,433,878 B1 | 8/2002 | Niu et al. | |
| 6,538,731 B2 | 3/2003 | Niu et al. | |
| 6,778,273 B2 | 8/2004 | Norton et al. | |
| 6,785,638 B2 | 8/2004 | Niu et al. | |
| 6,891,626 B2 | 5/2005 | Niu et al. | |
| 6,943,900 B2 | 9/2005 | Niu et al. | |
| 7,064,829 B2 | 6/2006 | Li et al. | |
| 7,280,229 B2 | 10/2007 | Li et al. | |
| 7,342,641 B2 * | 3/2008 | Sogard | 355/55 |
| 7,414,794 B2 * | 8/2008 | Novak | 359/649 |
| 2004/0267397 A1 | 12/2004 | Doddi et al. | |
| 2005/0192914 A1 | 9/2005 | Drege et al. | |
| 2005/0209816 A1 | 9/2005 | Vuong et al. | |

OTHER PUBLICATIONS

U.S. Appl. No. 12/050,053, filed Mar. 17, 2008 Tian et al.
U.S. Appl. No. 12/050,919, filed Mar. 18, 2008 for Tian et al.
U.S. Appl. No. 12/057,316, filed Mar. 27, 2008 for Tian et al.
U.S. Appl. No. 12/057,332, filed Mar. 27, 2008 for Tian et al.
U.S. Appl. No. 12/057,346, filed Mar. 27, 2008 for Tian et al.
U.S. Appl. No. 12/059,610, filed Mar. 31, 2008 for Meng et al.
U.S. Appl. No. 12/141,754, filed Jun. 18, 2008 for Tian et al.
U.S. Appl. No. 12/141,867, filed Jun. 18, 2008 for Tian et al.

* cited by examiner

*Primary Examiner*—Tu T Nguyen

(57) ABSTRACT

An Integrated Metrology Sensor (IMS) including a plurality of Field Replaceable Units (FRUs) for measuring a target on a wafer. The FRU configurations can be optimized to include the appropriate elements, so that each FRU can be pre-aligned and calibrated in the factory to minimize the time need to swap the FRU in the field due to failure or scheduled maintenance. The FRU configuration of the IMS is optimized to shorten the time to repair a failure or perform scheduled maintenance and increase the system reliability.

17 Claims, 5 Drawing Sheets

FIELD REPLACEABLE UNITS (FRUS) OPTIMIZED FOR INTEGRATED METROLOGY (IM)

BACKGROUND OF THE INVENTION

1. Field of the Invention

The present invention relates to integrated optical metrology, and more particularly to improving the integrated optical metrology serviceability and availability by optimizing the design of Field Replaceable Units (FRU) for the integrated optical metrology system.

2. Description of the Related Art

In the manufacturing of integrated circuits, very thin lines or holes down to 45 nm or sometimes smaller are patterned into photoresist and then transferred using an etching process into a layer of material below on a silicon wafer. It is extremely important to inspect and control the width and profile (also known as critical dimensions or CDs) of these lines or holes. Traditionally the inspection of CDs that are smaller than the wavelength of visible light has been done using expensive and slow scanning electron microscopes (CD-SEM) since all measurements are done in vacuum. As the structures get smaller and smaller, the process tolerance is getting tighter and tighter. Hence the required measurement precision and accuracy also becomes tighter and tighter. The measurement frequency and throughput also need to increase in order to monitor the process condition in real time. CD-SEM cannot meet the many CD metrology requirements in those areas due to its low throughput and limited CD profiling capability. In many cases, manufacturers need to measure CD and profiles immediately after the photoresist has been patterned, a non-destructive metrology is needed to avoid photoresist damage induced by e-beam in CD-SEM. For real time process control or advanced process control (APC), the measurement module needs to be integrated with process equipment, such as wafer track that develops the photoresist or etcher.

One measurement technique that has promise for non-destructive and fast CD measurements is scatterometry. Exemplary scatterometry techniques are described in U.S. Pat. No. 6,538,731, entitled "System and Method for Characterizing Macro-Grating Test Patterns in Advanced Lithography and Etch Processes", by Niu, et al., issued on Mar. 25, 2003, and is incorporated in its entirety herein by reference. Exemplary scatterometry techniques are described in U.S. Pat. No. 6,433,878, entitled "Method and Apparatus for the Determination of Mask Rules Using Scatterometry", by Niu, et al., issued on Apr. 13, 2002, and is incorporated in its entirety herein by reference. This technique takes advantage of the fact that small periodic lines or holes diffract an incident light beam, and the properties of the light in each of the diffraction orders carries information of the lines and holes. In practice, the optical properties of zero-th diffraction order that is reflected (or, for transparent samples, transmitted) from the periodic structures are measured with an optical metrology sensor, and measured data is analyzed with an analysis software, such as ODP. In performing scatterometry measurement, the intensities of the reflected or transmitted beam at various polarization states are measured versus wavelength, and in some cases, versus angle of incidence of the beam.

Optical metrology sensor measures the optical properties of the features on a wafer. These optical properties include the intensity and polarization state of reflected beam. These techniques are described in U.S. Pat. No. 7,064,829, entitled "Generic Interface for an Optical Metrology System", by Li, et al., issued on Jun. 20, 2006, and are incorporated in its entirety herein by reference. The optical metrology sensor can be designed to sense one or more of this optical properties. For example, the tool that measures the intensity of reflected beam is called a reflectometer, and tools that measure the polarization change are called ellipsometers. The optical metrology sensor typically uses photometric or spectral photometric detectors.

An optical metrology sensor involves directing an incident beam in one or more polarization states at a feature on a wafer, measuring the resulting diffraction signals, and measuring the signal from standard reflector in reflectometer case, the measured signs are first analyzed to find the optical properties of the feature, namely reflectivity or polarization state changes. The measured optical properties of the feature are analyzed to determine various characteristics of the feature. In semiconductor manufacturing, optical metrology is typically used for quality assurance, process control, and equipment control. For example, after fabricating a periodic grating in proximity to a semiconductor chip on a semiconductor wafer, an optical metrology system is used to determine the profile of the periodic grating. By determining the profile of the periodic grating, the quality of the fabrication process utilized to form the periodic grating, and by extension the semiconductor chip proximate the periodic grating, can be evaluated. Furthermore, the measured dimensions of features can be used to control the process equipment work conditions.

An integrated CD measurement tool must be both fast and compact, and must be non-destructive to the wafer under test. The wafer may also be loaded into the measurement tool at an arbitrary angle creating further complications for instruments that have a preferred measurement orientation with respect to certain wafer features.

Integrated metrology tools are needed for real time process control. The reliability and availability is paramount in this scheme. Any problem in metrology module will hinder process control and may cause process tool to stop. The maintenance time of the integrated metrology modules also need to be significantly reduced to minimize the downtime of the process tool and hence to maximize the availability of the process tool.

SUMMARY OF THE INVENTION

The invention presents an integrated metrology system (IMS) that is configured using a plurality of Field Replaceable Units (FRUs). The invention presents an IMS that can be constructed and used to measure CDs and overlay errors on periodic structures, and the IMS is compact and well suited for integration into a wafer process tool. The IMS has one or more FRUs that can be pre-aligned and calibrated so that it can be swapped in field with significantly reduced time.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Reliability, availability, and performance of semiconductor equipment are critical in a modern fabrication environment. The measured data from the integrated metrology system are used to monitor and control the process step the wafer in that process tool. A faulty in-line tool can cause throughput problems in the associated production line.

The present invention provides an optical Integrated Metrology Sensor (IMS) that uses Field Replaceable Units (FRUs) to improve tool reliability and availability. The FRU concept can be more easily applied when a new metrology tool is designed and constructed. The entire metrology system can be separated into many FRUs, and each one of the FRUs can be assembled, aligned, calibrated, installed, and/or replaced with a minimum amount of system level adjustment. In addition, there is a need to optimize the separation strategy/plan when defining and/or isolating the FRU from the entire IMS. It is noted that there is an optimized way to define/divide each FRU from the whole system. If the FRU is defined to be too large, the cost of replacing the FRU is high, and this can increase the cost of ownership of the optical metrology sensor. If the FRU is defined to be too small, it is more likely a system level adjustment will be needed when the FRU is replaced, and this can increase the cost of ownership of the optical metrology sensor.

An improved integrated metrology (IM) tool can be designed and built using varying sizes of FRUs. The inventor believes that the use of FRUs in an IM system can significantly minimize and/or substantially eliminate system level alignment, diagnostic and calibration procedures that are presently required after a scheduled maintenance is performed, and after fixing a system failure.

Figure 1:
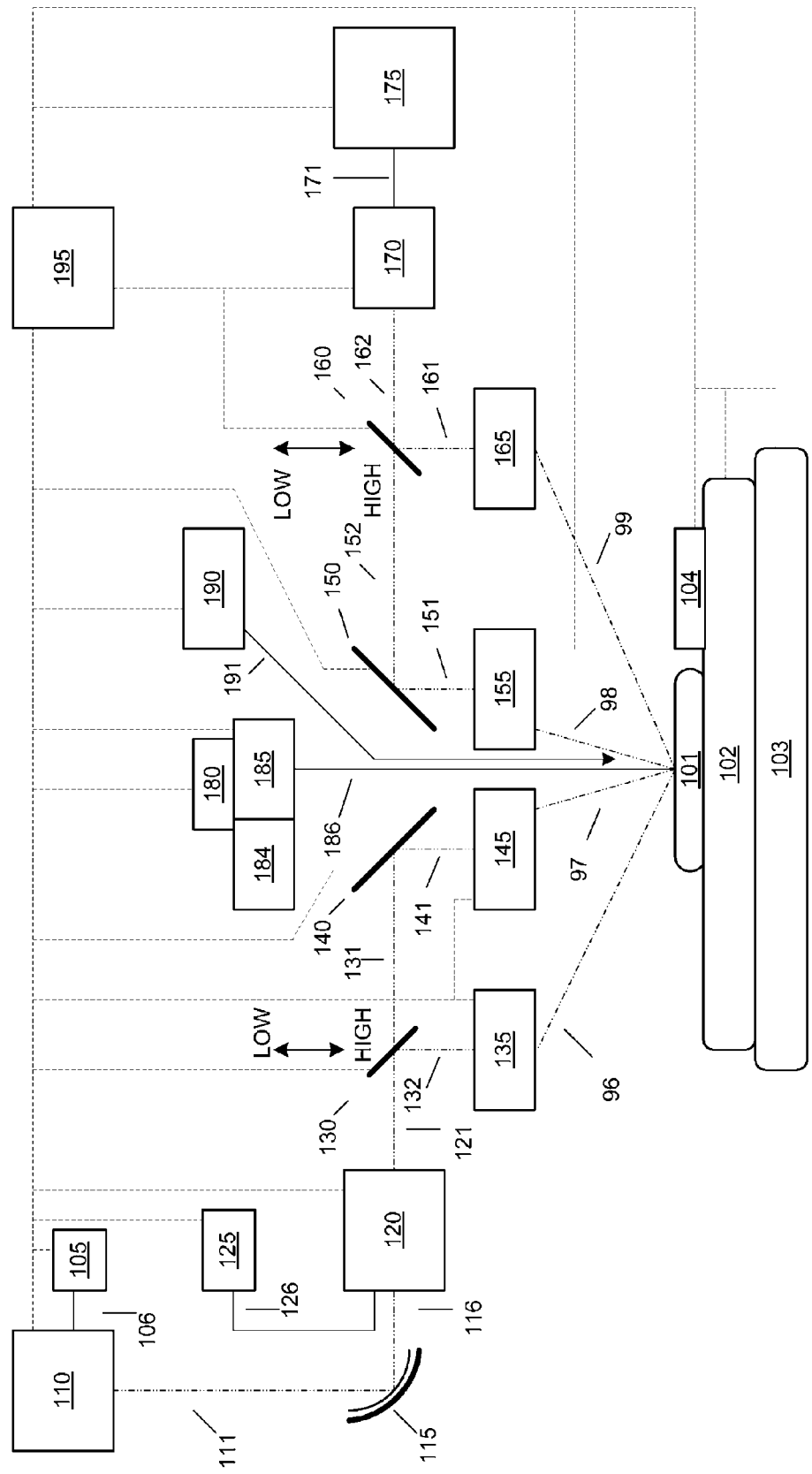
FIG. 1 depicts an exemplary optical metrology system in accordance with embodiments of the invention.

FIG. 1 shows an exemplary block diagram of an optical metrology system in accordance with embodiments of the invention. In the illustrated embodiment, an Integrated Metrology Sensor (IMS) 100 can have a platform subsystem 103, a wafer-positioning subsystem 102 and a wafer alignment sensor 104, One or more optical outputs 106 from the lamp subsystem 105 can be transmitted to an illuminator subsystem 110. One or more optical beams 111 can be sent from the illuminator subsystem 110 to a selector subsystem 115. The selector subsystem 115 can provide one or more optical beams 116 to a beam generator subsystem 120. In addition, a reference subsystem 125 can provide one or more reference beams to and/or exchange data with the beam generator subsystem 120 using path 126.

The IMS 100 can comprise a first selectable reflection subsystem 130 that can be used to direct one or more outputs 121 from the beam generator subsystem 120 as first outputs 131 when operating in a first mode "HIGH" or as second outputs 132 when operating in a second mode "LOW". When the first selectable reflection subsystem 130 is operating in the first mode "HIGH", one or more of the outputs 131 from the first selectable reflection subsystem 130 can be directed to a first reflection subsystem 140, and one or more outputs 141 from the first reflection subsystem 140 can be directed to a high angle focusing subsystem 145. When the first selectable reflection subsystem 130 is operating in the second mode "LOW", one or more of the second outputs 132 from the first selectable reflection subsystem 130 can be directed to a low angle focusing subsystem 135. Alternatively, other modes may be used and other configurations may be used.

When the IMS 100 is operating in the first mode "HIGH", one or more of the beams 97 from the high angle focusing subsystem 145 can be directed to the wafer 101. When the IMS 100 is operating in the second mode "LOW", one or more of the beams 96 from the low angle focusing subsystem 135 can be directed to the wafer 101. Alternatively, other modes may be used and other configurations may be used.

The IMS 100 can comprise a high angle collection subsystem 155, a low angle collection subsystem 165, a second reflection subsystem 150, and a second selectable reflection subsystem 160.

When the IMS 100 is operating in the first mode "HIGH", one or more of the beams 98 from the wafer 101 can be directed to the high angle collection subsystem 155. In addition, the high angle collection subsystem 155 can process the beams 98 obtained from the wafer 101 and high angle collection subsystem 155 can provide outputs 151 to the second reflection subsystem 150, and the second reflection subsystem 150 can provide reflected outputs 152 to the second selectable reflection subsystem 160. When the second selectable reflection subsystem 160 is operating in the first mode "HIGH", the reflected outputs 152 from the second reflection subsystem 150 can be directed to the analyzer subsystem 170. For example, one or more blocking elements can be moved allowing the reflected outputs 152 from the second reflection subsystem 150 to pass through without loss.

When the IMS 100 is operating in the second mode "LOW", one or more of the beams 99 from the wafer 101 can be directed to the low angle collection subsystem 165. In addition, the low angle collection subsystem 165 can process the beams 99 obtained from the wafer 101 and low angle collection subsystem 165 can provide outputs 161 to the second selectable reflection subsystem 160. When the second selectable reflection subsystem 160 is operating in the second mode "LOW", the outputs 162 from the second selectable reflection subsystem 160 can be directed to the analyzer subsystem 170.

When the IMS 100 is operating in the first mode "HIGH", high incident angle data from the wafer 101 can be analyzed using the analyzer subsystem 170, and when the IMS 100 is operating in the second mode "LOW", low incident angle data from the wafer 101 can be analyzed using the analyzer subsystem 170.

The IMS 100 can include one or more detection subsystems 175 that can receive inputs from the analyzer subsystem 170. One or more of detection subsystems 175 can include one or more spectrometers. For example, the spectrometers can operate from the Deep-Ultra-Violet to the visible regions of the spectrum.

The IMS 100 can include one or more camera subsystems 180, one or more illumination and imaging subsystems 185 coupled to one or more of the camera subsystems 180. In addition, the IMS 100 can also include one or more illuminator subsystems 184 that can be coupled to one or more of the imaging subsystems 185.

In some embodiments, the IMS 100 can include one or more auto-focusing subsystems 190 and auto-focusing beams 191.

One or more of the controllers (not shown) in one or more of the subsystems (105, 110, 115, 120, 125, 130, 135, 140, 145, 150, 155, 160, 165, 170, 175, 180, 185 and 190) can be used when performing real-time or non-real-time procedures. A controller can receive real-time or non-real-time data to update subsystem, processing element, process, recipe, profile, image, pattern, and/or model data. One or more of the subsystems (105, 110, 115, 120, 125, 130, 135, 140, 145, 150, 155, 160, 165, 170, 175, 180, 185 and 190) can exchange data using one or more Semiconductor Equipment Communications Standard (SECS) messages, can read and/or remove information, can feed forward, and/or can feedback the information, and/or can send information as a SECS message.

Those skilled in the art will recognize that one or more of the subsystems (105, 110, 115, 120, 125, 130, 135, 140, 145, 150, 155, 160, 165, 170, 175, 180, 185, and 190) can include computers and memory components (not shown) as required. For example, the memory components (not shown) can be used for storing information and instructions to be executed by computers (not shown) and may be used for storing temporary variables or other intermediate information during the execution of instructions by the various computers/processors in the IMS 100. One or more of the subsystems (105, 110, 115, 120, 125, 130, 135, 140, 145, 150, 155, 160, 165, 170, 175, 180, 185, and 190) can include the means for reading data and/or instructions from a computer readable medium and can comprise the means for writing data and/or instructions to a computer readable medium. The IMS 100 can perform a portion of or all of the processing steps of the invention in response to the computers/processors in the processing system executing one or more sequences of one or more instructions contained in a memory and/or received using a computer-readable medium. Such instructions may be received from another computer, a computer readable medium, or a network connection. In addition, one or more of the subsystems (105, 110, 115, 120, 125, 130, 135, 140, 145, 150, 155, 160, 165, 170, 175, 180, 185, and 190) can comprise control applications, Graphical User Interface (GUI) components, and/or database components. For example, the control applications can include Advanced Process Control (APC) applications, Fault Detection and Classification (FDC), and/or Run-to-Run (R2R) applications. In some embodiments, APC applications, FDC applications, and/or R2R applications can be performed using multi-angle metrology procedures.

In some embodiments, the IMS 100 can include Optical Digital Profilometry (ODP) elements (not shown), and ODP elements/systems are available from Timbre Technologies, Inc. (a Tokyo Electron Limited company). Alternatively, other data analysis elements for the metrology systems may be used. For example, ODP techniques can be used to obtain real-time data that can include critical dimension (CD) data, gate structure data, thickness data, and the wavelength ranges for the ODP data can range from less than approximately 45 nm to greater than approximately 900 nm. Exemplary ODP elements can include Optical Digital Profilometry Profiler Library elements, Profiler Application Server (PAS) elements, and other ODP Profiler Software elements. The ODP Profiler Library elements can comprise application specific database elements of optical spectra and its corresponding semiconductor profiles, critical dimensions (CDs), and film thicknesses. The PAS elements can comprise at least one computer that connects with optical hardware and computer network. The PAS elements can be configured to provide the data communication, ODP library operation, results generation, results analysis, and results output. The ODP Profiler Software elements can include the software installed on PAS elements to manage measurement recipe, ODP Profiler library elements, ODP Profiler data, ODP Profiler search/match results, ODP Profiler calculation/analysis results, data communication, and PAS interface to various metrology elements and computer network.

The IMS 100 can use polarizing reflectometry, spectroscopic ellipsometry, spectroscopic reflectometry, or other optical measurement techniques to accurately measure the profiles, CDs, and film thickness of the features on the wafer. The integrated data process (ODP) can be executed as an integrated data analyzer in an integrated group of subsystems. In addition, the integrated group (iODP) that consists of IMS 100 and data analyzer (ODP) into a process tool eliminates the need to break the wafer for performing the analyses or waiting for long periods for data from external systems. iODP techniques can be integrated with TEL processing systems and/or lithography systems and etch systems to provide real-time process monitoring and control.

An exemplary ODP is described in U.S. Pat. No. 6,943,900, entitled GENERATION OF A LIBRARY OF PERIODIC GRATING DIFFRACTION SIGNAL, by Niu, et al., issued on Sep. 13, 2005, and is incorporated in its entirety herein by reference.

Simulated diffraction signals with ODP can be generated by applying Maxwell's equations and using a numerical analysis technique to solve Maxwell's equations. For example, various numerical analysis techniques, including variations of rigorous coupled wave analysis (RCWA), can be used with multi-layer structures. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

An alternative procedure for generating a library of simulated-diffraction signals can include using a machine learning system (MLS). Prior to generating the library of simulated-diffraction signals, the MLS is trained using known input and output data. In one exemplary embodiment, simulated diffraction signals can be generated using a MLS employing a machine learning algorithm, such as back-propagation, radial basis function, support vector, kernel regression, and the like. For a more detailed description of machine learning systems and algorithms, see "U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In various embodiments, one or more of the subsystems (105, 110, 115, 120, 125, 130, 135, 140, 145, 150, 155, 160, 165, 170, 175, 180, 185, and 190) can perform evaluation, inspection, temperature control, alignment, verification, and/or storage on one or more wafers. For example, wafer data that can include wafer thickness, wafer curvature, layer thickness, wafer uniformity, pattern data, damage data, or particle data, or any combination thereof. In addition, controller 195 can determine if the wafer has been processed correctly or if a rework is required.

The IMS 100 data can include measured, predicted, and/or simulated data associated with patterns or structures, and the data can be stored using processing, wafer, lot, recipe, site, or wafer location data. the data can include variables associated with patterned structure profile, metrology device type and associated variables, and ranges used for the variables floated in the modeling and values of variables that were fixed in the modeling. The library data may include fixed and/or variable profile parameters (such as CD, sidewall angle, refractive index (n) data and extinction coefficient (k) data), and/or metrology device parameters (such as wavelengths, angle of incidence, and/or azimuth angle). For example, context and/or identification information such as sensor ID, site ID, wafer ID, slot ID, lot ID, recipe, state, and patterned structure ID may be used for organizing and indexing data.

Controller 195 can include coupling means 196 that can be used to couple the IMS 100 to other systems in a factory environment. In some examples, controller 195 may be configured to use factory level intervention and/or judgment rules to determine which processes are monitored and which data can be used. In addition, factory level intervention and/or judgment rules can be used to determine how to manage the data when a process can be changed, paused, and/or stopped. In addition, controller 195 can provide configuration information and update information.

Figure 2:
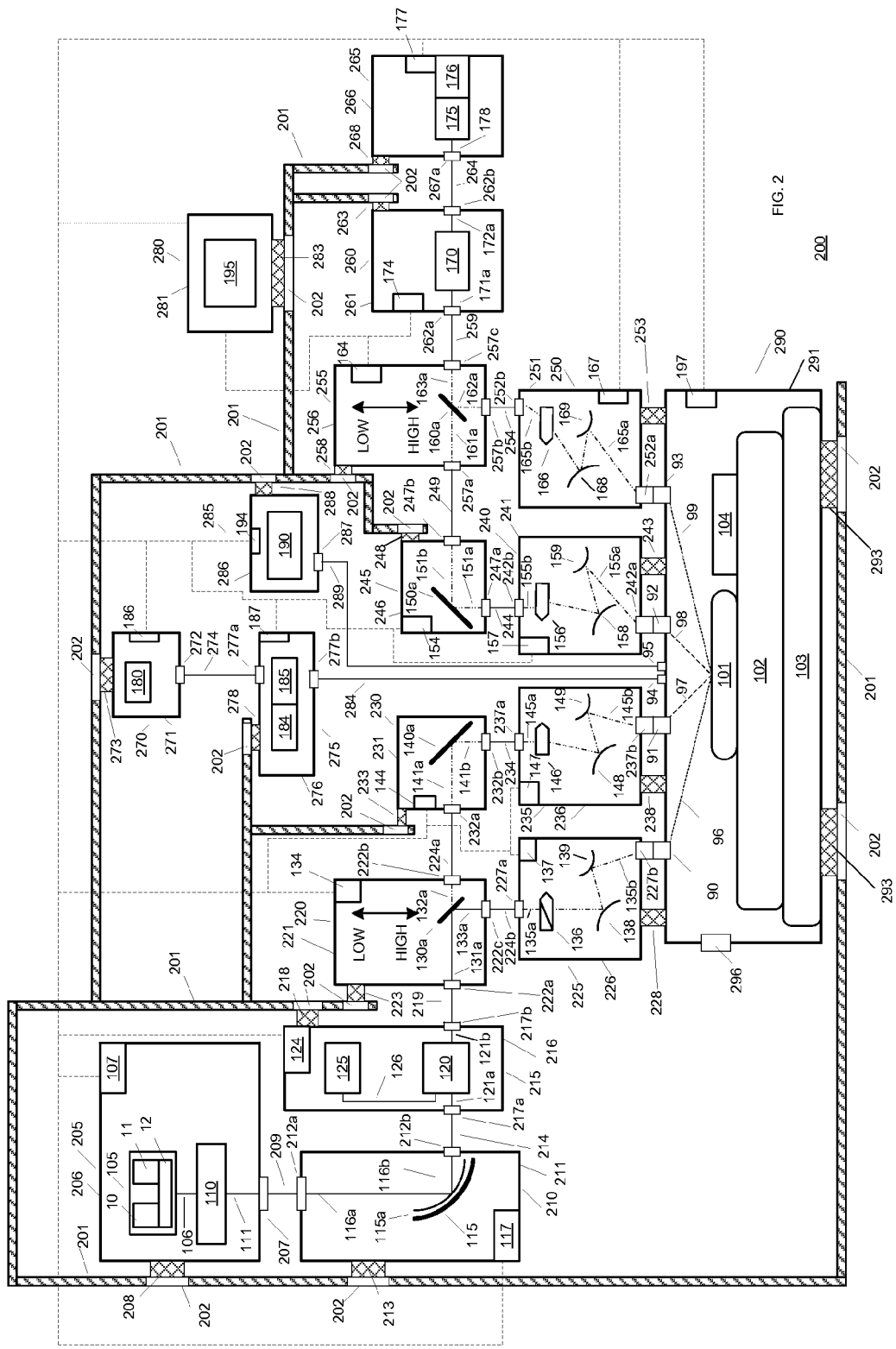
FIG. 2 shows an exemplary block diagram of an optical Integrated Metrology Sensor (IMS) including pre-aligned and/or calibrated Field Replaceable Units (FRUs) in accordance with embodiments of the invention.

FIG. 2 shows an exemplary block diagram of an Integrated Metrology Sensor (IMS) including Field Replaceable Units (FRUs) in accordance with embodiments of the invention. In the illustrated embodiment, a first configuration for the IMS 200 is shown. Alternatively, a different configuration may be used, and a different number of FRUs may be configured differently. Data and/or messages can be sent from and/or received by the FRUs can be used in the FRUs to optimize the process accuracy and precision. Data can be passed to FRUs in real-time as real-time variable parameters, overriding current recipe or model default values, improving the alignment time for the tool, and improving the measurement accuracy. FRUs can be used with a library-based system, or regression-based system, or any combination thereof.

The IMS 200 can be used to examine and analyze a structure formed on a wafer. Alternatively, other configurations may be used. The illustrated IMS 200 can be used to determine the profile of a target structure (not shown) formed on wafer 101. The target structure can be formed in test areas on wafer 101, such as adjacent to a device formed on wafer 101. In other embodiments, target structure can be formed in an area of the device that does not interfere with the operation of the device or along scribe lines on wafer 101.

Reliability, availability, throughput, and performance are important parameters for semiconductor equipments. Typically, most of the optical metrology systems for thin-film and critical dimension (CD) measurement are performed using stand-alone equipment and off-line applications for process monitor. As the semiconductor roadmap goes to smaller and smaller nodes, the tightened tolerances provide additional challenges on semiconductor process control. Integrated Metrology systems that are designed using FRUs can be used to more accurately measure the smaller structures created on the wafer, and can use the measured data either to optimize the process tools used to make the wafer structures, or for adjusting the process tool conditions for further processing of the wafer. When integrated metrology tools are incorporated into a manufacturing environment, the integrated metrology tools must have an increased reliability, an increased throughput, an increased availability, and a decreased repair time.

FRUs can be used to improve tool reliability, to reduce the time to repair, and to provide improved tool availability. FRUs can easily be used when new equipment is designed. Many different IMSs can be configured using FRUs that are configured differently. Each one of the FRUs can be assembled, aligned, calibrated, and swapped with a minimum amount of system level adjustment. To optimize cost and minimize system level adjustments, the IMS can be constructed using large, medium, and small FRUs.

Those skilled in the art will recognize that one or more of the controllers (107, 117, 124, 134, 137, 144, 147, 154, 157, 164, 167, 174, 177, 184, 187, 194, 195, and 197) can include microprocessors and memory components (not shown) as required. For example, the memory components (not shown) can be used for storing information and instructions to be executed by microprocessors (not shown) and may be used for storing temporary variables or other intermediate information during the execution of instructions by the various computers/processors in the IMS 200. One or more of the controllers (107, 117, 124, 134, 137, 144, 147, 154, 157, 164, 167, 174, 177, 184, 187, 194, 195, and 197) can include the means for reading data and/or instructions from a computer readable medium and can comprise the means for writing data and/or instructions to a computer readable medium. The IMS 200 can perform a portion of or all of the processing steps of the invention in response to the computers/processors in the IMS 200 executing one or more sequences of one or more instructions contained in a memory and/or received using a computer-readable medium. Such instructions may be received from another computer, a computer readable medium, or a network connection.

One or more of the FRUs (205, 210, 215, 220, 225, 230, 235, 240, 245, 250, 255, 260, 265, 270, 275, 280, 285, and 290) can comprise library components (not shown), Graphical User Interface (GUI) components (not shown), and/or database components (not shown). In addition, one or more of the FRUs (205, 210, 215, 220, 225, 230, 235, 240, 245, 250, 255, 260, 265, 270, 275, 280, 285, and 290) can perform Advanced Process Control (APC) applications, Fault Detection and Classification (FDC) applications, Run-to-Run (R2R) applications, Double-Patterning (D-P) procedures, and/or Double-Exposure (D-E) procedures.

When one or more of the FRUs (205, 210, 215, 220, 225, 230, 235, 240, 245, 250, 255, 260, 265, 270, 275, 280, 285, and 290) includes adjustable components, these components can be adjusted to compensate for drift and/or system variations, to eliminate the adjustment of the other FRUs, and to reduce the number of system level alignments.

A compact chassis assembly 201 can be constructed that can include pre-aligned mounting devices 202 for each of the FRUs (205, 210, 215, 220, 225, 230, 235, 240, 245, 250, 255, 260, 265, 270, 275, 280, 285, and 290) so that each FRU can be easily installed or removed without removing the other FRUs. The pre-aligned mounting devices 202 can be at predetermined points and can be used to align the FRUs and minimize the amount of system level testing when an FRU is replaced.

When FRUs are created, the FRUs can be used in an IMS that can be integrated with other processing tools. The IMS and the FRUs are designed to be highly reliable, to have a reasonable cost, and to be easily replaced to minimize the amount of tool downtime. FRUs are designed to have short diagnostic times, short maintenance times, and to minimize system level alignment times. In addition, FRUs can be designed to be aligned, tested, calibrated, and stored off-line for later use in a future scheduled maintenance procedures, or to quickly fix a system failure without requiring a system level alignment.

One or more of the FRUs can be designed and fabricated using sealed chambers (closed units) and a vacuum environment can be established within the sealed chamber, and optically transparent windows can be provided in one or more of the chamber walls. For example, one or more fused silica windows can be used. Alternatively, other materials may be used. The sealed chambers can be used to protect the wafer 101 from particles generated from the moving optics, and to protect the optics from out-gassing from the wafer 101.

When FRUs are used in the IMS 200, one or more of the characterization parameters can be associated with each one of the FRUs. The characterization parameters can be used to select the components required for the FRUs, can be used to determine how to assemble the selected components, and can be used to calibrate and test the FRUs. The characterization parameters can include generalized characterization parameters and FRU specific characterization parameters. For example, the generalized characterization parameters can include can include lifetime data, repair data, replacement data, calibration data, preventive maintenance data, actual operational data, required operational data, dimensional data, historical data, or real-time data, or any combination thereof associated with the components used in each FRU.

One or more sets of characterization parameters can be established when the FRU is constructed and/or repaired, and other sets of characterization parameters can be used when the FRU is calibrated and/or pre-aligned.

During and/or after some of the construction and/or repair procedures, one or more of the characterization parameters associated with an FRU can be used in calibration/pre-alignment procedures to create a calibrated (pre-aligned) FRU. In some embodiments, one or more of the calibration/pre-alignment procedures can be performed while the FRU is configured within the IMS 200. In other embodiments, the FRU is configured to be easily removed from the IMS 200 and attached to the optical test bench (410, FIG. 4) in an optical test subsystem (400, FIG. 4) using attachment elements.

During a maintenance procedure, one or more replacement FRUs can be pre-aligned and/or calibrated before being installed in the IMS 100, and new characterization parameters can be established for each replacement FRU. A replacement FRU can be created when one or more of the components in the FRU are replaced, repaired, and/or realigned. The new characterization parameters can include new lifetime data, new repair data, new replacement data, new calibration data, new preventive maintenance data, new actual operational data, new required operational data, new dimensional data, new historical data, or new real-time data, or any combination thereof associated with the components used in each replacement FRU.

The wafer-positioning FRU 290 can include a wafer-positioning chamber 291, one or more optical connection devices (90, 91, 92, 93, 94, and 95) mounted in one or more walls of the wafer-positioning chamber 291, a controller 197, and one or more attachment elements 293 configured for coupling the wafer-positioning FRU 290 to the compact chassis assembly 201. Each optical connection devices (90, 91, 92, 93, 94, and 95) can operate using one or more sets of wavelengths. For example, the optical connection devices (90, 91, 92, 93, 94, and 95) can include optical windows, optical fibers, and/or other devices.

A wafer-positioning FRU 290 can comprise a platform subsystem 103, a wafer-positioning subsystem 102 coupled to the platform subsystem 103, and a wafer alignment sensor 104 coupled to the wafer-positioning subsystem 102. The wafer-positioning FRU 290 can be configured to support, clamp, align, and/or translate the wafer 101. The wafer-positioning FRU 290 can include a translation port 296 for transferring the wafer 101 into and/or out of the wafer-positioning chamber 291.

In some embodiment, the wafer-positioning FRU 290 can include X-Y stages to move the wafer 101. For example, a reduced motion stage may be used with or without wafer stage θ rotation, or a polar coordinate (R, θ) stage can be used to reduce the footprint required by the IMS 200. A complete 360-degree rotating range can be used, although a 180-degree range may be acceptable in many cases. For example, one or more driver motors (not shown) may be used.

When the source FRU 205 is installed in the IMS 200, the source FRU 205 can provide one or more optical beams 111 to the selector FRU 210. The source FRU 205 can include a chamber 206, one or more output optical connection devices 207, and one or more attachment elements 208 for coupling the FRU 205 to the compact chassis assembly 201. In addition, the source FRU 205 can comprise one or more lamp subsystems 105, one or more controllers 107, one or more illuminator subsystems 110, and one or more optical outputs 106 from the lamp subsystem 105 can be transmitted internally to the illuminator subsystem 110. Alternatively, additional subsystems may be included.

The lamp subsystem 105 can include a high-pressure xenon lamp 10 that can provide illumination between 220 nm and 1100 nm. The lamp subsystem 105 can also include a deuterium lamp and selection component 12 to provide deep-UV light between 190 nm and 340 nm. The shorter wavelength UV light can provide better results on smaller structures. Alternatively, other white light sources may be included. In some configurations, the lamp lifetime can be typically ~2000 hours.

A selection component 12 can include one or more reflecting surfaces (not shown) that can be used to select between the two light sources (10 and 11). In addition, the illuminator subsystems 110 can be used to turn-on and/or turn-off one or more of the beams from the lamp subsystem 105. The illuminator subsystems 110 can be used to protect the optics from excessive UV light and to allow the measurement of a background signal. The illuminator subsystems 110 can create one or more optical beams 111 that are large enough to illuminate one or more output optical connection devices 207 and one or more multi-mode optical fibers 209. One or more of these fibers 209 can have a core diameter of 100 microns.

In the existing stand-alone metrology systems, the optical sources are designed as an integral part of the system, and the entire metrology system can be off-line for an extended period of time during maintenance. In addition, the new lamp must be physically aligned to the system to compensate the lamp-to-lamp variations. In some cases, the other components of the system also need to be adjusted, and oftentimes a system re-calibration is required. The existing procedures may take a day typically, and can be much longer when some difficulty is encountered.

When a failure has occurred in a calibrated source FRU 205 in the IMS 200, the failed source FRU can be replaced by a replacement source FRU that has been pre-calibrated and/or pre-aligned. The characterization parameters associated with the failed source FRU 205 or the replacement source FRU can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data for one or more of the light sources (10, 11) or other components in the source FRU 205.

Figure 4:
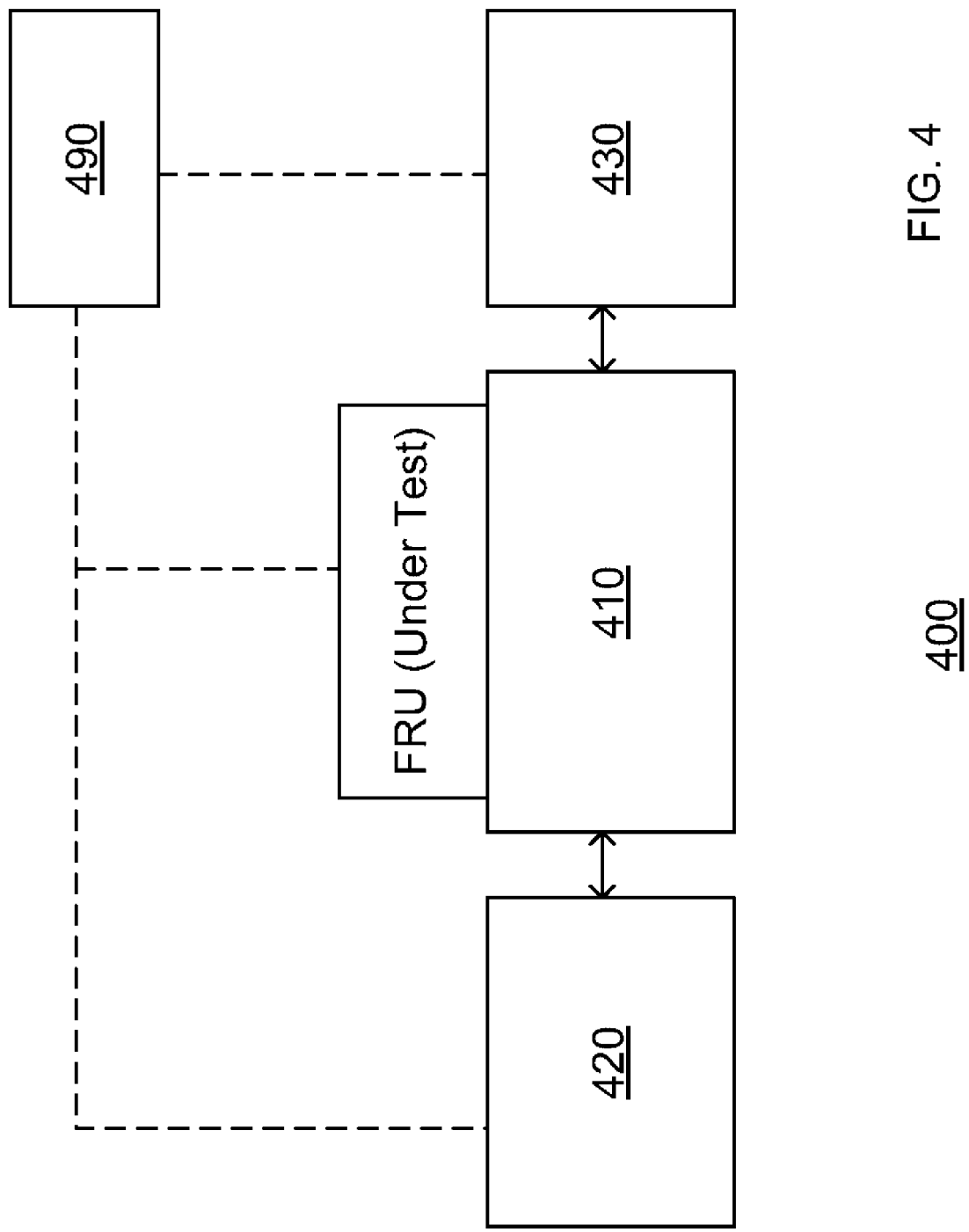
FIG. 4 illustrates a simplified block diagram of a test subsystem in accordance with embodiments of the invention.

One or more of the controllers (107, 195) can be used for storing characterization parameters and operational data for the source FRU 205 and/or executing operational and calibration procedures using the characterization parameters for the source FRU 205, and can be used to control the calibrated source FRU 205 when the source FRU 205 is coupled in the IMS 200 or to an optical test bench (410, FIG. 4) in an optical test subsystem (400, FIG. 4). In addition, the controller 107 can perform monitoring procedures that can be used to provide warning data or failure data that can be used to initiate a replacement procedure during operating or calibrating procedures. When a new FRU is installed in the IMS 200 or when a new component is installed in the source FRU 205, the controller (107, 195) can be programmed to compensate for the system level variations, and a system level maintenance procedure may not be required. For example, the lamp subsystems 105 and the illuminator subsystems 110 can be adjusted to reduce or eliminate the adjustment of the other components of the IMS 200 and the need to re-calibrate the IMS 200.

When the source FRU 205 is being constructed and/or repaired, the lamp subsystem 105, the illuminator subsystems 110 can be mounted and aligned within the chamber 206; the output optical connection devices 207 can be mounted and aligned in one or more of the chamber walls; and the chamber 206 can be evacuated and sealed.

The source FRU 205 can be coupled to the selector FRU 210 using the optical connection devices (207 and 212a) and one or more optical fibers 209. In other configurations, the source FRU 205 can be coupled to the selector FRU 210 using one or more optically transparent windows when the optical connection devices (207 and 212a) include optically transparent windows. For example, one or more optical beams 111 can be sent from the illuminator subsystem 110 in the source FRU 205 to a selector subsystem 115 in the selector FRU 210.

When the selector FRU 210 is installed in the IMS 200, the selector FRU 210 can receive one or more input beams 116a from the source FRU 205, can provide one or more output beams 116b to the beam generator FRU 215. One or more of the beams (116a and 116b) can include one or more reference beams and/or one or more measurement beams. When pre-calibrated and/or pre-aligned FRUs (205, 210) are used, pre-calibrated and/or pre-aligned beams (116a, 116b) can be established.

The selector FRU 210 can comprise a chamber 211, one or more input optical connection devices 212a, one or more output optical connection devices 212b, a controller 117, and one or more attachment elements 213 for coupling the selector FRU 210 to the compact chassis assembly 201. When the selector FRU 210 is being constructed and/or repaired, the curved low-loss reflection surfaces 115a can be mounted and aligned within the chamber 211; the input optical connection devices 212a, and the output optical connection devices 212b can be mounted and aligned in one or more of the chamber walls; and the chamber 211 can be evacuated and sealed.

When a failure has occurred in a calibrated selector FRU 210 in the IMS 200, the failed selector FRU 210 can be replaced by a replacement selector FRU that has been pre-calibrated and/or pre-aligned. The characterization parameters associated with the failed and/or the replacement selector FRU 210 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, or the expected and/or actual loss data, or any combination thereof for one or more of the curved low-loss reflection surfaces 115a, the chamber 211, the input optical connection devices 212a, and the output optical connection devices 212b or another component in the selector FRU 210.

One or more of the controllers (117, 195) can be used for storing characterization parameters and operational data for the selector FRU 210 and/or for executing operational and calibration procedures using the characterization parameters for the selector FRU 210. The controllers (117, 195) can also be used to control the calibrated selector FRU 210 when the selector FRU 210 is coupled in the IMS 200 or to an optical test bench (410, FIG. 4) in an optical test subsystem (400, FIG. 4). In addition, the controller 117 can perform monitoring procedures that can be used to provide warning data or failure data that can be used to initiate a replacement procedure during operating or calibrating procedures. When a new FRU is installed in the IMS 200 or when a new component is installed in the selector FRU 210, the controllers (117, 195) can be programmed to compensate for the system level variations, and a system level maintenance procedure may not be required. For example, the lamp subsystems 105, the illuminator subsystems 110, or the curved low-loss reflection surfaces 115a can be adjusted to reduce or eliminate the adjustment of the other components of the IMS 200 and the need to re-calibrate the IMS 200.

The selector FRU 210 can be coupled to the beam generator FRU 215 using the optical connection devices (212b and 217a) and one or more optical fibers 214. In other configurations, the selector FRU 210 can be coupled to the beam generator FRU 215 using one or more optically transparent windows when the optical connection devices (212b and 217a) include optically transparent windows.

When the beam generator FRU 215 is installed in the IMS 200, the beam generator FRU 215 can receive one or more input beams 121a from the selector FRU 210, can provide one or more output beams 121b to the first beam selector FRU 220. One or more of the beams (121a and 121b) can include one or more reference beams and/or one or more measurement beams. When pre-calibrated and/or pre-aligned FRUs (210, 215) are used, pre-calibrated and/or pre-aligned beams (121a, 121b) can be established.

The beam generator FRU 215 can comprise a chamber 216, one or more input optical connection devices 217a, one or more output optical connection devices 217b, a controller 124, and one or more attachment elements 218 for coupling the beam generator FRU 215 to the compact chassis assembly 201. In addition, the beam generator FRU 215 can comprise one or more beam generator subsystems 120 and one or more reference subsystems 125. Alternatively, additional subsystems may be included. One or more of the reference subsystems 125 can provide one or more reference beams to and/or exchange data with the beam generator subsystem 120 using path 126. For example, the beam generator subsystems 120, the reference subsystems 125, or the controller 124 can perform measurement functions so that the beam generator FRU 215 can be pre-aligned before it is installed in the IMS 200 during a shortened maintenance cycle.

When the beam generator FRU 215 is being constructed and/or repaired, the beam generator subsystem 120, the reference subsystem 125, can be aligned and mounted within the chamber 211; the input optical connection devices 217a, and the output optical connection devices 217b can be aligned and mounted in one or more of the walls of the chamber 211; and the chamber 211 can be evacuated and sealed.

When a failure has occurred in a calibrated beam generator FRU 215 in the IMS 200, the failed beam generator FRU 215 can be replaced by a replacement beam generator FRU that has been pre-calibrated and/or pre-aligned. The characterization parameters associated with the failed and/or replacement beam generator FRU 215 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, or the expected and/or actual loss data, or any combination thereof for the beam generator subsystem 120, the reference subsystem 125, the chamber 216, the input optical connection devices 217a, and the output optical connection devices 217b, the optical fiber 214, or other components in the beam generator FRU 215.

One or more of the controllers (124, 195) can be used for storing characterization parameters and operational data for the beam generator FRU 215 and/or for executing operational and calibration procedures using the characterization parameters for the beam generator FRU 215. The controllers (124, 195) can also be used to control the calibrated beam generator FRU 215 when the beam generator FRU 215 is coupled in the IMS 200 or to an optical test bench (410, FIG. 4) in an optical test subsystem (400, FIG. 4). In addition, the controller 124 can perform monitoring procedures that can be used to provide warning data or failure data that can be used to initiate a replacement procedure during operating or calibrating procedures. When a new FRU is installed in the IMS 200 or when a new component is installed in the beam generator FRU 215, the controllers (124, 195) can be programmed to compensate for the system level variations, and a system level maintenance procedure may not be required. For example, the beam generator subsystem 120, or the reference subsystem 125 can be adjusted to reduce or eliminate the adjustment of the other components of the IMS 200 and the need to re-calibrate the IMS 200.

The beam generator FRU 215 can be coupled to the first beam selector FRU 220 using the optical connection devices (217b and 222a) and one or more optical fibers 219. In other embodiments, the beam generator FRU 215 can be coupled to the first beam selector FRU 220 using one or more optically transparent windows when the optical connection devices (217b and 222a) include optically transparent windows. For example, one or more optical beams 121b can be sent from one or more beam generator FRU 215 to one or more of the first beam selector FRUs 220.

When the first beam selector FRU 220 is operating in the IMS 200, the first beam selector FRU 220 can receive one or more first input beams 131a from the beam generator FRU 215, can provide one or more first output beams 132a to the first beam reflection FRU 220 during a first mode, and can provide one or more low angle reflected beams 133a to the low angle focusing FRU 225 during a second mode. When pre-calibrated and/or pre-aligned FRUs (215, 220) are used, pre-calibrated and/or pre-aligned beams (131a, 132a, 133a) can be established.

The first beam selector FRU 220 can comprise a chamber 221, one or more input optical connection devices 222a, one or more first output optical connection devices 222b, one or more second output optical connection devices 222c, a controller 134, and one or more attachment elements 223 for coupling the first beam selector FRU 220 to the compact chassis assembly 201. The first beam selector FRU 220 can comprise one or more first low-loss reflecting surfaces 130a that can be used to allow the first input beam 131a to pass through to the first output optical connection devices 222b when the IMS 200 is operating in the first mode (HIGH) and that can be used to direct the first input beam 131a to the second output optical connection devices 222c when the IMS 200 is operating in the second mode (LOW). One or more of the first low-loss reflecting surfaces 130a can be a first surface convex mirror, or a concave fused silica mirror. The first low-loss reflecting surfaces 130a can be used to correct the aberrations so that the low angle reflected beam 133a has near diffraction-limited quality from 190 nm to 1100 nm. For example, one or more of the first low-loss reflecting surfaces 130a can be moved to a first position when the IMS 200 is operating in the first mode (LOW), and one or more of the first low-loss reflecting surfaces 130a can be moved to a second position when the IMS 200 is operating in the second mode (HIGH). In addition, additional components (not shown) can be included that can perform sensing, positioning, reflecting, summing, and/or focusing functions as required.

When the first beam selector FRU 220 is being constructed and/or repaired, the first low-loss reflecting surfaces 130a can be aligned and mounted within the chamber 221; the input optical connection devices 222a, the first output optical connection devices 222b and the second output optical connection devices 222c can be aligned and mounted in one or more walls of the chamber 221; and the chamber 226 can be evacuated and sealed.

When a failure has occurred in a calibrated first beam selector FRU 220 in the IMS 200, the failed first beam selector FRU 220 can be replaced by a replacement first beam selector FRU that has been pre-calibrated and/or pre-aligned. The characterization parameters associated with the failed and/or replacement first beam selector FRU 220 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, or the expected and/or actual loss data, or any combination thereof for the first low-loss reflecting surfaces 130a, the chamber 221, the input optical connection devices 222a, and the output optical connection devices (222b and 222c), the optical fiber 219, or other components in the first beam selector FRU 220.

One or more of the controllers (134, 195) can be used for storing characterization parameters and operational data for the first beam selector FRU 220 and/or for executing operational and calibration procedures using the characterization parameters for the first beam selector FRU 220. The controllers (134, 195) can also be used to control the calibrated first beam selector FRU 220 when the first beam selector FRU 220 is coupled in the IMS 200 or to an optical test bench (410, FIG. 4) in an optical test subsystem (400, FIG. 4). In addition, the controller 134 can perform monitoring procedures that can be used to provide warning data or failure data that can be used to initiate a replacement procedure during operating or calibrating procedures. When a new FRU is installed in the IMS 200 or when a new component is installed in the first beam selector FRU 220, the controllers (134, 195) can be programmed to compensate for the system level variations, and a system level maintenance procedure may not be required. For example, the first low-loss reflecting surfaces 130a, the chamber 221, the input optical connection devices 222a, the output optical connection devices (222b and 222c), or the optical fiber 219 can be adjusted to reduce or eliminate the adjustment of the other components of the IMS 200 and the need to re-calibrate the IMS 200.

The first beam selector FRU 220 can be coupled to the first beam reflection FRU 230 using the optical connection devices (222b and 232a) and one or more optical fibers 224a. In other embodiments, the first beam selector FRU 220 can be coupled to the first beam reflection FRU 230 using one or more optically transparent windows when the optical connection devices (222b and 232a) include optically transparent windows. In addition, the first beam selector FRU 220 can be coupled to the low angle focusing FRU 225 using the optical connection devices (222c and 227a) and one or more optical fibers 224b. In other embodiments, the first beam selector FRU 220 can be coupled to the low angle focusing FRU 225 using one or more optically transparent windows when the optical connection devices (222b and 227a) include optically transparent windows.

When a low angle focusing FRU 225 is installed in the IMS 200, the low angle focusing FRU 225 can receive one or more low angle input beams 135*a* from the first beam selector FRU 220 and can provide a low angle focused beam 135*b* to the wafer-positioning FRU 290. When pre-calibrated and/or pre-aligned FRUs (220, 225) are used, pre-calibrated and/or pre-aligned beams (135*a*, 135*b*) can be established.

The low angle focusing FRU 225 can comprise a chamber 226, one or more input optical connection devices 227*a*, one or more output optical connection devices 227*b*, one or more attachment elements 228 for coupling the low angle focusing FRU 225 to one or more walls of the wafer-positioning chamber 291, and a controller 137.

The low angle focusing FRU 225 can also include one or more polarizers 136 that can linearly polarize the light before the light is incident onto the wafer 101, and the polarization can be selected to maximize the sensitivity of the optical measurement to the parameters of the sample. In some examples, one or more of the polarizers 136 can provide the S-polarized light onto the wafer 101. In other examples, a polarizer 136 may be rotated when collecting additional measurement data. In addition, a first set of highly reflective curved surfaces (138 and 139) can be used to fold the light path so that the non-normal incidence angles do not lead to unnecessarily large footprint for the first beam selector FRU 220. The smaller footprint allows the first beam selector FRU 220 to be used in a compact IMS 200. One or more of the highly reflective curved surfaces (138 and 139) can be a first surface convex mirror, or a concave fused silica mirror. In addition, the two highly reflective curved surfaces (138 and 139) can be used to correct the aberrations so that the low angle focused beam 135*b* has near diffraction-limited quality from 190 nm to 1100 nm. In addition, additional components (not shown) can be included that can perform positioning, measuring, reflecting, summing, and/or focusing functions as required.

For example, the light sent to the wafer can be focused and imaged by the first set of highly reflective curved surfaces (138 and 139). In addition, the polarizer 136 may be configured to have beam-splitting properties and can be made from alpha barium borate. For example, a beam may be split into S-polarized light, and P-polarized light. Some of the optical fibers used in the IMS 200 can have smaller core diameters than other fibers so that the measurements are not overly sensitive to focus. In various configurations, the diameter of optical fibers or optical windows can be used to determine the geometric size of the measurement spot on the wafer 101.

When the low angle focusing FRU 225 is being constructed and/or repaired, the polarizers 136, and the first set of highly reflective curved surfaces (138 and 139) can be aligned and mounted within the chamber 226; the input optical connection devices 227*a* and the output optical connection devices 227*b* can be mounted in one or more of the walls of the chamber 226; and the chamber 226 can be evacuated and sealed.

When a failure has occurred in a calibrated low angle focusing FRU 225 in the IMS 200, the failed low angle focusing FRU can be replaced by a replacement low angle focusing FRU that has been pre-calibrated and/or pre-aligned. The characterization parameters associated with the failed and/or replacement first low angle focusing FRU 225 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the polarizers 136, the first set of highly reflective curved surfaces (138 and 139), the chamber 226, the input optical connection devices 227*a*, and the output optical connection devices 227*b*, the optical fiber 224*b*, or other components in the low angle focusing FRU 225.

One or more of the controllers (137, 195) can be used for storing characterization parameters and operational data for the low angle focusing FRU 225 and/or for executing operational and calibration procedures using the characterization parameters for the low angle focusing FRU 225. The controllers (137, 195) can also be used to control the calibrated low angle focusing FRU 225 when the low angle focusing FRU 225 is coupled in the IMS 200 or to an optical test bench (410, FIG. 4) in an optical test subsystem (400, FIG. 4). In addition, the controller 137 can perform monitoring procedures that can be used to provide warning data or failure data that can be used to initiate a replacement procedure during operating or calibrating procedures. When a new FRU is installed in the IMS 200 or when a new component is installed in the low angle focusing FRU 225, the controllers (137, 195) can be programmed to compensate for the system level variations, and a system level maintenance procedure may not be required. For example, the polarizers 136, the first set of highly reflective curved surfaces (138 and 139), the chamber 226, the input optical connection devices 227*a*, the output optical connection devices 227*b*, and the optical fiber 224*b* can be adjusted to reduce or eliminate the adjustment of the other components of the IMS 200 and the need to re-calibrate the IMS 200.

The low angle focusing FRU 225 can be coupled to the wafer-positioning FRU 290 using the optically transparent windows. In other embodiments, the low angle focusing FRU 225 can be coupled to the wafer-positioning FRU 290 using one or more optical fibers. For example, one or more low angle focused beams 135*b* can be sent from the low angle focusing FRU 225 as a low angle incident beam 96 to a measurement spot on a wafer in the wafer-positioning FRU 290 when the IMS 200 is operating in a second mode (LOW). In addition, the low angle incident beam 96 can have an angle of incidence that can between approximately 45 degrees and approximately 80 degrees from a normal vector perpendicular to a wafer surface. Alternatively, the low angle focusing FRU 225 can include one or more movable mirrors.

When a first beam reflection FRU 230 is installed in the IMS 200, the first beam reflection FRU 230 can receive one or more input beams 141*a* from the first beam selector FRU 220 and can provide one or more high angle reflected beam 141*b* to the high angle focusing FRU 235. Alternatively, additional subsystems may be included. One or more of the beams (141*a* and 141*b*) can include one or more reference beams and/or one or more measurement beams. When pre-calibrated and/or pre-aligned FRUs (220, 230) are used, pre-calibrated and/or pre-aligned beams (141*a*, 141*b*) can be established.

The first beam reflection FRU 230 can comprise a chamber 231, one or more input optical connection devices 232*a* mounted in a wall of the chamber 231, one or more output optical connection devices 232*b* mounted in a wall of the chamber 221, a controller 144, and one or more attachment elements 233 for coupling the first beam reflection FRU 230 to the compact chassis assembly 201.

The first beam reflection FRU 230 can also comprise one or more second low-loss reflecting surfaces 140*a* that can be used to allow the input beam 141*a* to pass through to the output optical connection devices 232*b* when the metrology system is operating in the first mode (HIGH). One or more of the second low-loss reflecting surfaces 140a can be a first surface convex mirror, or a concave mirror. The second low-loss reflecting surfaces 140a can be used to correct aberrations so that the high angle reflected beam 141b has near diffraction-limited quality from 190 nm to 1100 nm. In addition, additional components (not shown) can be included that can perform reflecting, summing, and/or focusing functions as required.

When the first beam reflection FRU 230 is being constructed and/or repaired, the second low-loss reflecting surfaces 140a can be aligned and mounted within the chamber 231; the input optical connection devices 232a and the output optical connection devices 232b can be mounted in one or more of the walls of the chamber 231; and the chamber 231 can be evacuated and sealed.

When a failure has occurred in a calibrated first beam reflection FRU 230 in the IMS 200, the failed first beam reflection FRU can be replaced by a replacement first beam reflection FRU that has been pre-calibrated and/or pre-aligned. The characterization parameters associated with the failed and/or replacement first beam reflection FRU 230 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the second low-loss reflecting surfaces 140a, the chamber 231, the input optical connection devices 232a, and the output optical connection devices 232b, the optical fiber 224a, or other components in the first beam reflection FRU 230.

One or more of the controllers (144, 195) can be used for storing characterization parameters and operational data for the first beam reflection FRU 230 and/or for executing operational and calibration procedures using the characterization parameters for the first beam reflection FRU 230. The controllers (144, 195) can also be used to control the calibrated first beam reflection FRU 230 when the first beam reflection FRU 230 is coupled in the IMS 200 or to an optical test bench (410, FIG. 4) in an optical test subsystem (400, FIG. 4). In addition, the controller 144 can perform monitoring procedures that can be used to provide warning data or failure data that can be used to initiate a replacement procedure during operating or calibrating procedures. When a new FRU is installed in the IMS 200 or when a new component is installed in the first beam reflection FRU 230, the controllers (144, 195) can be programmed to compensate for the system level variations, and a system level maintenance procedure may not be required. For example, second low-loss reflecting surfaces 140a, the chamber 231, the input optical connection devices 232a, the output optical connection devices 232b, and the optical fiber 224a can be adjusted to reduce or eliminate the adjustment of the other components of the IMS 200 and the need to re-calibrate the IMS 200.

The first beam reflection FRU 230 can be coupled to the high angle focusing FRU 235 using the optical connection devices (232b and 237a) and one or more optical fibers 234. In other embodiments, the first beam reflection FRU 230 can be coupled to the high angle focusing FRU 235 using one or more optically transparent windows when the optical connection devices (232b and 237a) include optically transparent windows. For example, one or more high angle reflected beams 141b can be sent from the first beam reflection FRU 230 to the high angle focusing FRU 235 when the IMS 200 is operating in a first mode (HIGH).

When the high angle focusing FRU 235 is installed in the IMS 200, the high angle focusing FRU 235 can receive one or more high angle input beams 145a from the first beam reflection FRU 230 and can provide one high angle focused beams 145b to the wafer-positioning FRU 290. When pre-calibrated and/or pre-aligned FRUs (220, 225) are used, pre-calibrated and/or pre-aligned beams (135a, 135b) can be established.

The high angle focusing FRU 235 can comprise a chamber 236, one or more input optical connection devices 237a, one or more output optical windows 237b, one or more attachment elements 238 for coupling the high angle focusing FRU 235 to one or more walls of the wafer-positioning chamber 291, and a controller 147. The high angle focusing FRU 235 can also include one or more polarizers 146 that can linearly polarize the light before the beam is incident onto the wafer 101, and the polarization can be selected to maximize the sensitivity of the optical measurement to the parameters of the sample. In some examples, one or more of the polarizers 146 can provide the S-polarized light onto the wafer 101. In other examples, a polarizer 146 may be rotated to collect additional measurement data. In addition, a second set of highly reflective curved surfaces (148 and 149) can be used to fold the light path so that the non-normal incidence angles do not lead to unnecessarily large footprint for the high angle focusing FRU 235. A small footprint is desirable so that the high angle focusing FRU 235 can be used in a compact IMS 200. One or more of the reflecting surfaces can be a first surface convex mirror, or a concave fused silica mirror. The second set of highly reflective curved surfaces (148 and 149) can be used to correct aberrations so that the high angle focused beam 145b has near diffraction-limited quality from 190 nm to 1100 nm. In addition, additional components (not shown) can be included that can perform positioning, reflecting, summing, and/or focusing functions as required.

In some configurations, the light beam can be focused and imaged by the second set of highly reflective curved surfaces (148 and 149) before being sent to the wafer. In addition, the polarizer 146 may be configured to have beam-splitting properties and can be made from alpha barium borate. For example, a beam may be split into S-polarized light, and P-polarized light. Some of the optical fibers used in the IMS 200 can have smaller core diameters than other fibers so that the measurements are not overly sensitive to focus. In various configurations, the diameter of optical fibers or optical windows can be used to determine the geometric size of the measurement spot on the wafer 101.

When the high angle focusing FRU 235 is constructed and/or repaired, the polarizers 146 and the second set of highly reflective curved surfaces (148 and 149) can be mounted within the chamber 236; the input optical connection devices 237a and the output optical windows 237b can be mounted in one or more of the chamber walls; and the chamber 236 can be evacuated and sealed.

When a failure has occurred in a calibrated high angle focusing FRU 235 in the IMS 200, the failed high angle focusing FRU can be replaced by a replacement high angle focusing FRU that has been pre-calibrated and/or pre-aligned. The characterization parameters associated with the failed and/or replacement high angle focusing FRU 235 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the polarizers 146 and the second set of highly reflective curved surfaces (148 and 149), the chamber 236, the input optical connection devices 237a, and the output optical connection devices 237b, the optical fiber 234, or other components in the high angle focusing FRU 235.

One or more of the controllers (147, 195) can be used for storing characterization parameters and operational data for the high angle focusing FRU 235 and/or for executing operational and calibration procedures using the characterization parameters for the high angle focusing FRU 235. The controllers (147, 195) can also be used to control the calibrated high angle focusing FRU 235 when the high angle focusing FRU 235 is coupled in the IMS 200 or to an optical test bench (410, FIG. 4) in an optical test subsystem (400, FIG. 4). In addition, the controller 147 can perform monitoring procedures that can be used to provide warning data or failure data that can be used to initiate a replacement procedure during operating or calibrating procedures. When a new FRU is installed in the IMS 200 or when a new component is installed in the high angle focusing FRU 235, the controllers (147, 195) can be programmed to compensate for the system level variations, and a system level maintenance procedure may not be required. For example, the polarizers 146 and the second set of highly reflective curved surfaces (148 and 149), the chamber 236, the input optical connection devices 237a, and the output optical connection devices 237b, the optical fiber 234 can be adjusted to reduce or eliminate the adjustment of the other components of the IMS 200 and the need to re-calibrate the IMS 200.

The high angle focusing FRU 235 can be coupled to the wafer-positioning FRU 290 using the optically transparent windows. In other embodiments, the high angle focusing FRU 235 can be coupled to the wafer-positioning FRU 290 using one or more optical fibers. For example, one or more high angle focused beams 145b can be sent from the high angle focusing FRU 235 as a high angle incident beam 97 to a measurement spot on a wafer in the wafer-positioning FRU 290 when the IMS 200 is operating in a first mode (HIGH). In addition, high angle incident beam 97 can have an angle of incidence that can be between approximately 15 degrees and approximately 50 degrees for a normal vector perpendicular to the wafer surface. Alternatively, the high angle focusing FRU 235 can include one or more movable mirrors.

When the high angle collecting FRU 240 is installed in the IMS 200, the high angle collecting FRU 240 can receive one or more input beams 155a from the wafer-positioning FRU 290 and can provide one high angle output beams 155b to the second beam reflection FRU 245. The high angle collecting FRU 240 can comprise a chamber 241, one or more input optical connection devices 242a, one or more output optical connection devices 242b, one or more attachment elements 238 for coupling the high angle collecting FRU 240 to one or more walls of the wafer-positioning chamber 291, and a controller 157. When pre-calibrated and/or pre-aligned FRUs (290, 240) are used, pre-calibrated and/or pre-aligned beams (155a, 155b) can be established.

The high angle collecting FRU 240 can include one or more polarizers 156 that can linearly polarize the light after the beam is reflected from the wafer 101, and the polarization can be selected to maximize the sensitivity of the optical measurement to the parameters of the sample. In some examples, one or more of the polarizers 156 can provide the S-polarized light. In other examples, a polarizer 156 may be rotated to collect additional measurement data. In addition, a third set of highly reflective curved surfaces (158 and 159) can be used to fold the light path so that the non-normal incidence angles do not lead to unnecessarily large footprint for the high angle collecting FRU 240. A small footprint allows the high angle collecting FRU 240 to be used in a compact IMS 200. One or more of the reflecting surfaces can be a first surface convex mirror, or a concave fused silica mirror. The third set of highly reflective curved surfaces (158 and 159) can be used to correct aberrations so that the high angle output beam 155b has near diffraction-limited quality from 190 nm to 1100 nm. In addition, additional components (not shown) can be included that can perform positioning, reflecting, summing, and/or focusing functions as required.

In some embodiments, the high angle collecting FRU 240 can receive one or more high-angle diffracted beams 98 from the wafer surface as a high-angle input beam 155a. The light sent from the wafer (high-angle input beam 155a) can be collected and imaged by the third set of highly reflective curved surfaces (158 and 159). In addition, the polarizer 156 may be configured to have beam-splitting properties and can be made from alpha barium borate. For example, a beam may be split into S-polarized light, and P-polarized light. Some of the optical fibers used in the metrology system can have smaller core diameters than other fibers so that the measurements are not overly sensitive to focus. In various configurations, the diameter of optical fibers or optical windows can be used to determine the geometric size of the measurement spot on the wafer 101.

When the high angle collecting FRU 240 is being constructed and/or repaired, the polarizers 156 and the third set of highly reflective curved surfaces (158 and 159) can be aligned and mounted within the chamber 241; the input optical connection devices 242a and the output optical connection devices 242b can be mounted in one or more of the chamber walls; and the chamber 241 can be evacuated and sealed.

When a failure has occurred in a calibrated high angle collecting FRU 240 in the IMS 200, the failed high angle collecting FRU can be replaced by a replacement high angle collecting FRU that has been pre-calibrated and/or pre-aligned. The characterization parameters associated with the failed and/or replacement high angle collecting FRU 240 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the polarizers 156 and the third set of highly reflective curved surfaces (158 and 159), the chamber 241, the input optical connection devices 242a, and the output optical connection devices 242b, or other components in the high angle collecting FRU 240.

One or more of the controllers (157, 195) can be used for storing characterization parameters and operational data for the high angle collecting FRU 240 and/or for executing operational and calibration procedures using the characterization parameters for the high angle collecting FRU 240. The controllers (157, 195) can also be used to control the calibrated high angle collecting FRU 240 when the high angle collecting FRU 240 is coupled in the IMS 200 or to an optical test bench (410, FIG. 4) in an optical test subsystem (400, FIG. 4). In addition, the controller 157 can perform monitoring procedures that can be used to provide warning data or failure data that can be used to initiate a replacement procedure during operating or calibrating procedures. When a new FRU is installed in the IMS 200 or when a new component is installed in the high angle collecting FRU 240, the controllers (157, 195) can be programmed to compensate for the system level variations, and a system level maintenance procedure may not be required. For example, the polarizers 156 and the third set of highly reflective curved surfaces (158 and 159), the chamber 241, the input optical connection devices 242a, and the output optical connection devices 242b can be adjusted to reduce or eliminate the adjustment of the other components of the IMS 200 and the need to re-calibrate the IMS 200.

The high angle collecting FRU 240 can be coupled to the wafer-positioning FRU 290 using the optically transparent windows. In other embodiments, the high angle collecting FRU 240 can be coupled to the wafer-positioning FRU 290 using one or more optical fibers. For example, one or more high angle diffracted beams 98 can be reflected from the measurement spot on a wafer in the wafer-positioning FRU 290 to high angle collecting FRU 240 when the IMS 200 is operating in a first mode (HIGH). In addition, the high angle diffracted beam 98 can have a reflection angle that can be between approximately 15 degrees and approximately 50 degrees from a normal vector perpendicular to the wafer surface. Alternatively, the high angle collecting FRU 240 can include one or more movable mirrors.

When the second beam reflection FRU 245 is installed in the IMS 200, the second beam reflection FRU 245 can receive one or more high angle collection beams 151a from the high angle collecting FRU 240 and can provide one or more high angle reflected beams 151b to the second beam selector FRU 255. One or more of the beams (151a and 151b) can include one or more reference beams and/or one or more measurement beams. When pre-calibrated and/or pre-aligned FRUs (240, 245) are used, pre-calibrated and/or pre-aligned beams (151a, 151b) can be established.

The second beam reflection FRU 245 can comprise a chamber 246, one or more input optical connection devices 247a, one or more output optical connection devices 247b, a controller 154, and one or more attachment elements 248 for coupling the second beam reflection FRU 245 to the compact chassis assembly 201. Alternatively, additional subsystems may be included.

The second beam reflection FRU 245 can include one or more third low-loss reflecting surfaces 150a that can be used to direct the high angle collection beam 151a to the output optical connection devices 247b when the metrology system is operating in the first mode (HIGH). One or more of the third low-loss reflecting surfaces 150a can be a first surface convex mirror, or a concave fused silica mirror. The third low-loss reflecting surfaces 150a can be used to correct aberrations so that the high angle reflected beam 151b has near diffraction-limited quality from 190 nm to 1100 nm. In addition, additional components (not shown) can be included that can perform positioning, reflecting, summing, and/or focusing functions as required.

When the second beam reflection FRU 245 is being constructed and/or repaired, the third low-loss reflecting surfaces 150a can be aligned and mounted within the chamber 246; the input optical connection devices 247a and the output optical connection devices 247b can be aligned and mounted in one or more of the chamber walls; and the chamber 246 can be evacuated and sealed.

When a failure has occurred in a calibrated second beam reflection FRU 245 in the IMS 200, the failed second beam reflection FRU can be replaced by a replacement second beam reflection FRU that has been pre-calibrated and/or pre-aligned. The characterization parameters associated with the failed and/or replacement second beam reflection FRU 245 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the third low-loss reflecting surfaces 150a, the chamber 246, the input optical connection devices 247a, the output optical connection devices 247b, and the optical fiber 244, or other components in the second beam reflection FRU 245.

One or more of the controllers (154, 195) can be used for storing characterization parameters and operational data for the second beam reflection FRU 245 and/or for executing operational and calibration procedures using the characterization parameters for the second beam reflection FRU 245. The controllers (154, 195) can also be used to control the calibrated second beam reflection FRU 245 when the second beam reflection FRU 245 is coupled in the IMS 200 or to an optical test bench (410, FIG. 4) in an optical test subsystem (400, FIG. 4). In addition, the controller 154 can perform monitoring procedures that can be used to provide warning data or failure data that can be used to initiate a replacement procedure during operating or calibrating procedures. When a new FRU is installed in the IMS 200 or when a new component is installed in the second beam reflection FRU 245, the controllers (154, 195) can be programmed to compensate for the system level variations, and a system level maintenance procedure may not be required. For example, the third low-loss reflecting surfaces 150a, the chamber 246, the input optical connection devices 247a, and the output optical connection devices 247b, the optical fiber 244 can be adjusted to reduce or eliminate the adjustment of the other components of the IMS 200 and the need to re-calibrate the IMS 200.

The second beam reflection FRU 245 can be coupled to the second beam selector FRU 255 using the optical connection devices (247b and 257a) and one or more optical fibers 249. In other embodiments, the second beam reflection FRU 245 can be coupled to the second beam selector FRU 255 using one or more optically transparent windows when the optical connection devices (247b and 257a) include optically transparent windows. For example, one or more high angle reflected beams 151b can be sent from the second beam reflection FRU 245 to the second beam selector FRU 255 when the IMS 200 is operating in a first mode (HIGH).

When the low angle collecting FRU 250 is installed in the IMS 200, the low angle collecting FRU 250 can receive one or more input beams 165a from the wafer-positioning FRU 290 and can provide one or more low angle output beams 165b to the second beam selector FRU 255. One or more of the beams (165a and 165b) can include one or more reference beams and/or one or more measurement beams. When pre-calibrated and/or pre-aligned FRUs (250, 290) are used, pre-calibrated and/or pre-aligned beams (165a, 165b) can be established.

The low angle collecting FRU 250 can comprise a chamber 251, one or more input optical connection devices 252a, one or more output optical connection devices 252b, one or more attachment elements 253 for coupling the low angle collecting FRU 250 to one or more walls of the wafer-positioning chamber 291, and a controller 167. In various examples, the input optical connection devices (222a, 232a, 242a, and 252a) and the output optical connection devices (222b, 232b, 242b, and 252b) can include optical windows, optical fibers, and/or other optical devices that can be optically transparent in ranges from approximately 150 nm to approximately 1000 nm.

The low angle collecting FRU 250 can include one or more polarizers 166 that can linearly polarize the light after the beam is reflected from the wafer 101, and the polarization can be selected to maximize the sensitivity of the optical measurement to the parameters of the sample. In some examples, one or more of the polarizers 166 can provide the S-polarized light. In other examples, a polarizer 166 may be rotated to collect additional measurement data. In addition, a fourth set of highly reflective curved surfaces (168 and 169) can be used to fold the light path so that the non-normal incidence angles do not lead to unnecessarily large footprint for the low angle collecting FRU 250. The small footprint allows the low angle collecting FRU 250 to be used in a compact IMS 200 with other small FRUs. One or more of the fourth set of highly reflective curved surfaces (168 and 169) can be a first surface convex mirror, or a concave fused silica mirror. The highly reflective surfaces can be used to correct aberrations so that the low angle output beam 165*b* has near diffraction-limited quality from 190 nm to 1100 nm. In addition, additional components (not shown) can be included that can perform positioning, reflecting, summing, and/or focusing functions as required.

In some embodiments, the low angle collecting FRU 250 can receive one or more low angle diffracted beams 99 from the wafer surface as a low-angle input beam 165*a*, and the light reflected from the wafer (input beam 165*a*) can be collected and imaged the fourth set of highly reflective curved surfaces (168 and 169). For example, the low-angle input beam 165*a* can include one or more reference beams and/or one or more measurement beams from the wafer surface In addition, the polarizer 166 may be configured to have beam-splitting properties and can be made from alpha barium borate. For example, a beam may be split into S-polarized light, and P-polarized light. Some of the optical fibers used in the metrology system can have smaller core diameters than other fibers so that the measurements are not overly sensitive to focus. In various configurations, the diameter of optical fibers or optical windows can be used to determine the geometric size of the measurement spot on the wafer 101. A preventive maintenance procedure for the low angle collecting FRU 250 can be scheduled and can be based on the expected lifetime for a polarizer 166, the fourth set of highly reflective curved surfaces (168 and 169), and/or another component.

When the low angle collecting FRU 250 is constructed and/or repaired, the polarizers 166 and the fourth set of highly reflective curved surfaces (168 and 169) can be aligned and mounted within the chamber 261; the input optical connection devices 252*a* and the output optical connection devices 252*b* can be mounted and aligned in one or more of the chamber walls; and the chamber 261 can be evacuated and sealed.

When a failure has occurred in a calibrated low angle collecting FRU 250 in the IMS 200, the failed low angle collecting FRU can be replaced by a replacement low angle collecting FRU that has been pre-calibrated and/or pre-aligned. The characterization parameters associated with the failed and/or replacement low angle collecting FRU 250 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the polarizers 166 and the fourth set of highly reflective curved surfaces (168 and 169), the chamber 251, the input optical connection devices 252*a*, and the output optical connection devices 252*b*, or other components in the low angle collecting FRU 250.

One or more of the controllers (167, 195) can be used for storing characterization parameters and operational data for the low angle collecting FRU 250 and/or for executing operational and calibration procedures using the characterization parameters for the low angle collecting FRU 250. The controllers (167, 195) can also be used to control the calibrated low angle collecting FRU 250 when the low angle collecting FRU 250 is coupled in the IMS 200 or to an optical test bench (410, FIG. 4) in an optical test subsystem (400, FIG. 4). In addition, the controller 167 can perform monitoring procedures that can be used to provide warning data or failure data that can be used to initiate a replacement procedure during operating or calibrating procedures. When a new FRU is installed in the IMS 200 or when a new component is installed in the low angle collecting FRU 250, the controllers (167, 195) can be programmed to compensate for the system level variations, and a system level maintenance procedure may not be required. For example, the polarizers 166 and the fourth set of highly reflective curved surfaces (168 and 169), the chamber 251, the input optical connection devices 252*a*, and the output optical connection devices 252*b* can be adjusted to reduce or eliminate the adjustment of the other components of the IMS 200 and the need to re-calibrate the IMS 200.

The low angle collecting FRU 250 can be coupled to the wafer-positioning FRU 290 using the optically transparent windows. In other embodiments, the low angle collecting FRU 250 can be coupled to the wafer-positioning FRU 290 using one or more optical fibers. When two or more optically transparent windows are used, they must also be matched and aligned properly. For example, one or more low angle diffracted beams 99 can be sent from the measurement spot on a wafer in the wafer-positioning FRU 290 to the low angle collecting FRU 250 when the IMS 200 is operating in the second mode (LOW). In addition, the low angle diffracted beam 99 can have a reflection angle that can be between approximately 40 degrees and approximately 70 degrees from a normal vector perpendicular to the wafer surface. Alternatively, the low angle collecting FRU 250 can include one or more movable mirrors.

When the second beam selector FRUs 255 is installed in the IMS 200, the second beam selector FRUs 255 can receive one or more first input beams 161*a* from the second beam reflection FRU 245, can receive one or more second input beams 162*a* from low angle collecting FRU 250, and can provide one or more output beams 163*a* to the analyzer FRU 260. One or more of the beams (161*a*, 162*a*, and 163*a*) can include one or more reference beams and/or one or more measurement beams. When pre-calibrated and/or pre-aligned FRUs (245, 255) are used, pre-calibrated and/or pre-aligned beams (162*a*, 163*a*) can be established.

The second beam selector FRU 255 can comprise a chamber 256, one or more first input optical connection devices 257*a*, one or more second input optical connection devices 257*b*, one or more output optical connection devices 257*c*, a controller 164, and one or more attachment elements 258 for coupling the second beam selector FRU 255 to the compact chassis assembly 201.

The second beam selector FRU 255 can comprise one or more fourth low-loss reflecting surfaces 160*a* that can be used to allow the first input beam 161*a* to pass through to the output optical connection devices 257*c* when the metrology system is operating in the first mode (HIGH) and that can be used to direct the second input beam 162*a* to the output optical connection devices 257c when the metrology system is operating in the second mode (LOW) One or more of the fourth low-loss reflecting surfaces 160a can be a first surface convex mirror, or a concave fused silica mirror. The fourth low-loss reflecting surfaces 160a can be used to correct aberrations introduced so that the output beam 163a has near diffraction-limited quality from 190 nm to 1100 nm. For example, one or more of the fourth low-loss reflecting surfaces 160a can be moved to a first position when the IMS 200 is operating in the first mode (HIGH), and one or more of the fourth low-loss reflecting surfaces 160a can be moved to a second position when the IMS 200 is operating in the second mode (LOW). In addition, additional components (not shown) can be included that can perform positioning, reflecting, summing, and/or focusing functions as required.

When the second beam selector FRU 255 is constructed and/or repaired, the fourth low-loss reflecting surfaces 160a can be aligned and mounted within the chamber 256; the first input optical connection devices 257a, the second input optical connection devices 257b and the output optical connection devices 257c can be mounted in one or more of the chamber walls; and the chamber 256 can be evacuated and sealed.

When a failure has occurred in a calibrated second beam selector FRU 255 in the IMS 200, the failed second beam selector FRU 255 can be replaced by a replacement second beam selector FRU that has been pre-calibrated and/or pre-aligned. The characterization parameters associated with the failed and/or replacement second beam selector FRU 255 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the fourth low-loss reflecting surfaces 160a, the chamber 256, the input optical connection devices (257a, 257b), the output optical connection devices 257c, and the optical fibers (249, 254), or other components in the second beam selector FRU 255.

One or more of the controllers (164, 195) can be used for storing characterization parameters and operational data for the second beam selector FRU 255 and/or for executing operational and calibration procedures using the characterization parameters for the second beam selector FRU 255. The controllers (164, 195) can also be used to control the calibrated second beam selector FRU 255 when the second beam selector FRU 255 is coupled in the IMS 200 or to an optical test bench (410, FIG. 4) in an optical test subsystem (400, FIG. 4). In addition, the controller 164 can perform monitoring procedures that can be used to provide warning data or failure data that can be used to initiate a replacement procedure during operating or calibrating procedures. When a new FRU is installed in the IMS 200 or when a new component is installed in the second beam selector FRU 255, the controllers (164, 195) can be programmed to compensate for the system level variations, and a system level maintenance procedure may not be required. For example, fourth low-loss reflecting surfaces 160a, the chamber 256, the input optical connection devices (257a, 257b), the output optical connection devices 257c, and the optical fibers (249, 254) can be adjusted to reduce or eliminate the adjustment of the other components of the IMS 200 and the need to re-calibrate the IMS 200.

In some system configurations, the second beam selector FRU 255 can be coupled to the analyzer FRU 260 using the optical connection devices (257c and 262a) and one or more optical fibers 259. In other configurations, one or more optically transparent windows can be used when the optical connection devices (257c and 262a) include optically transparent windows.

When the analyzer FRU 260 is installed in the IMS 200, the analyzer FRU 260 can receive one or more first input beams 171a from the second beam selector FRU 255 and can provide one or more output beams 172a to the measurement FRU 265. When pre-calibrated and/or pre-aligned FRUs (255, 260) are used, pre-calibrated and/or pre-aligned beams (171a, 172a) can be established.

The analyzer FRU 260 can comprise a chamber 261, one or more first input optical connection devices 262a, one or more output optical connection devices 262b, and one or more attachment elements 263 for coupling the analyzer FRU 260 to the compact chassis assembly 201. In addition, the analyzer FRU 260 can comprise one or more analyzer subsystems 170, and a controller 174. For example, the analyzer FRU 260 can include one or more highly accurate beam analyzers. Alternatively, additional subsystems and/or components may be included. In some examples, the analyzer FRU 260 can comprise one or more multi-channel spectrometers that can measure the spectrum in several beams simultaneously. In addition, the analyzer FRU 260 can comprise multiple linear detector arrays or one or more two dimensional detector arrays.

When the IMS 200 is operating in the first mode "HIGH", one or more of the high-angle outputs from the wafer can be directed to the analyzer FRU 260 using the high angle collection FRU 240, the second beam reflection FRU 245, and the second beam selector FRU 255. When the IMS 200 is operating in the first mode "HIGH", a high angle of incidence can be used for one or more of the incident beams and one or more of the reflected beams. When the IMS 200 is operating in the second mode "LOW", one or more of the low-angle outputs from the wafer can be directed to the analyzer FRU 260 using the low angle collection FRU 250 and the second beam selector FRU 255. When the IMS 200 is operating in the second mode "LOW", a low angle of incidence can be used for one or more of the incident beams and one or more of the reflected beams.

The analyzer FRU 260 can analyze one or more reference beams and/or one or more measurement beams from the surface of the wafer. The analyzer FRU 260 can include reflecting, summing, selecting, and/or analyzing components that are configured to operate over a wide range of wavelengths. A preventive maintenance procedure for the analyzer FRU 260 can be scheduled and may be based on a lifetime for a measurement device or a lamp lifetime. When a new measurement device is installed in the analyzer FRU 260, the controller 174 can be programmed to compensate for the variations caused by the new measurement device. In addition, if a new lamp is installed in the source FRU 205 associated with the analyzer FRU 260, the controller 174 can be programmed to compensate for the lamp-to-lamp variations. When one or more of the other components in the analyzer FRU 260 are replaced and/or adjusted, the controller 174 can be programmed to compensate for the replaced part and to perform adjustments as required.

When a failure has occurred in a calibrated analyzer FRU 260 in the IMS 200, the failed analyzer FRU can be replaced by a replacement analyzer FRU that has been pre-calibrated and/or pre-aligned. The characterization parameters associated with the failed and/or replacement analyzer FRU 260 can include the expected and/or actual lifetimes, the expected and/or actual repair/replacement times, the expected and/or actual calibration/measurement times, the expected and/or actual wavelength data, the expected and/or actual intensity data, the expected and/or actual beam width data, the expected and/or actual temperature data, the expected and/or actual adjustment ranges, the expected and/or actual polarization values, or the expected and/or actual loss data, or any combination thereof for the reflecting, summing, selecting, and/or analyzing components, the chamber 261, the input optical connection devices 262a, and the output optical connection devices 262s, the optical fibers (259, 264), or other components in the analyzer FRU 260.

The analyzer FRU 260 can be coupled to the measurement FRU 265 using the optical connection devices (262b and 267a) and one or more optical fibers 264. Alternatively, the analyzer FRU 260 can be coupled to the measurement FRU 265 using one or more optically transparent windows when the optical connection devices (262b and 267a) include optically transparent windows.

In alternate embodiments, the analyzer FRU 260 and measurement FRU 265 may be combined into a single FRU.

When the measurement FRU 265 is installed in the IMS 200, the measurement FRU 265 can receive one or more optical signals 178 from the analyzer FRU 260 and can provide data to the controller FRU 280.

The measurement FRU 265 can comprise a chamber 266, one or more input optical connection devices 267a mounted in a wall of the chamber 261, and one or more attachment elements 268 for coupling the measurement FRU 265 to the compact chassis assembly 201.

The measurement FRU 265 can comprise one or more detection subsystems 175, one or more databases 176, and one or more controllers 177. When the IMS 200 is operating in the first mode "HIGH", high incident angle data from the wafer 101 can be measured using the measurement FRU 265, and when the IMS 200 is operating in the second mode "LOW", low incident angle data from the wafer 101 can be measured using the measurement FRU 265. The measurement FRU 265 can comprise one or more spectrometers. For example, the spectrometers can operate from the Deep-Ultra-Violet to the visible regions of the spectrum.

The measurement FRU 265 can measure one or more reference beams and/or one or more measurement beams from the surface of the wafer. The measurement FRU 265 can include measuring, sensing, reflecting, summing, and/or selecting components that are configured to operate over a wide range of wavelengths.

When the measurement FRU 265 is used in the IMS 200, a preventive maintenance procedure for the measurement FRU 265 can be scheduled and may be based on a reference source lifetime or a measurement device lifetime. When a new FRU is installed in the IMS 200, the controller 177 can be programmed to compensate for the variations caused by the new FRU. In addition, if a new lamp is installed in the source FRU 205 associated with the analyzer FRU 260, the controller 177 can be programmed to compensate for the lamp-to-lamp variations. When one or more of the other components in the measurement FRU 265 are replaced and/or adjusted, the controller 177 can be programmed to compensate for the replaced part and to perform adjustments as required.

The measurement FRU 265 can use the measured data to determine the parameters of the target structure on the wafer at the measurement spot. The parameters can be the thicknesses of films, line width critical dimension (CD), the sidewall slope of lines, etc, and the data can be converted into spectral, absolute, polarized reflectance and compared to the spectrum library to find the best match and therefore the unknown structure parameters. There are many alternative approaches to process the measured data to yield structure parameters.

The camera FRU 270 can comprise a chamber 271, one or more output optical connection devices 272 mounted in a wall of the chamber 271, and one or more attachment elements 273 for coupling the camera FRU 270 to the compact chassis assembly 201. The camera FRU 270 can include one or more camera subsystems 180 and one or more controllers 186 that can be used to inspect and/or align the wafer 101.

The camera FRU 270 can receive one or more reference beams, one or more inspection beams, and/or one or more alignment beams from the surface of the wafer. The camera FRU 270 can include measuring, sensing, reflecting, summing, and/or selecting components that are configured to be compatible with light sources operating in the visible region or outside the visible region. When the camera FRU 270 is used in an IM system, a preventive maintenance procedure for the camera FRU 270 can be scheduled and may be based on a source lifetime or a sensing device lifetime. When a new FRU is installed in the IMS 200, the controller 186 can be programmed to compensate for the variations caused by the new FRU. In addition, when one or more of the components in the camera FRU 270 are replaced and/or adjusted, the controller 186 can be programmed to compensate for the replaced part and to perform adjustments as required.

The imaging FRU 275 can comprise a chamber 276, one or more input optical connection devices 277a mounted in a wall of the chamber 276, one or more output optical connection devices 277b mounted in a wall of the chamber 276, and one or more attachment elements 278 for coupling the imaging FRU 275 to the compact chassis assembly 201.

The imaging FRU 275 can comprise one or more one illuminator subsystems 184, one or more of the imaging subsystems 185, and one or more controllers 187. For example, one or more of the illuminator subsystems 184 can be coupled to one or more of the imaging subsystems 185 and can provide one or more sources of light having both visible and non-visible wavelengths.

The imaging FRU 275 can be coupled to the camera FRU 270 using the optical connection devices (272 and 277a) and one or more optical fibers 274. Alternatively, the imaging FRU 275 can be coupled to the camera FRU 270 using one or more optically transparent windows when the optical connection devices (272 and 277a) include optically transparent windows.

The imaging FRU 275 can be coupled to the wafer-positioning FRU 290 using the optical connection devices (277b and 94) and one or more optical fibers 284. Alternatively, imaging FRU 275 can be coupled to the wafer-positioning FRU 290 using one or more optically transparent windows when the optical connection devices (277b and 94) include optically transparent windows. For example, the imaging FRU 275 can be mounted next to and/or attached to the wafer-positioning chamber 291.

The imaging FRU 275 can include sourcing, measuring, sensing, reflecting, summing, and/or selecting components that are configured to operate over a wide range of wavelengths. When the measurement FRU 265 is used in the IMS 200, a preventive maintenance procedure for the measurement FRU 265 can be scheduled and may be based on a reference source lifetime or a measurement device lifetime. When a new FRU is installed in the IMS 200, the controller 177 can be programmed to compensate for the variations caused by the new FRU. In addition, if a new lamp is installed in the source FRU 205 associated with the analyzer FRU 260, the controller 177 can be programmed to compensate for the lamp-to-lamp variations. When one or more of the components in the measurement FRU 265 are replaced and/or adjusted, the controller 177 can be programmed to compensate for the replaced part and to perform adjustments as required.

The controller FRU 280 can comprise a chamber 281 and one or more attachment elements 283 for coupling the controller FRU 280 to the compact chassis assembly 201.

The controller FRU 280 can comprise one or more controllers 195 and one or more interface elements (not shown) that can be used to couple the IMS 200 to other systems in a factory environment. In some examples, controller 195 may be configured to use factory level intervention and/or judgment rules to determine which processes are monitored and which data can be used. In addition, factory level intervention and/or judgment rules can be used to determine how to manage the data when a process can be changed, paused, and/or stopped. In addition, controller 195 can provide configuration information and update information.

The auto-focusing FRU 285 can comprise a chamber 286, one or more optical connection devices 287 mounted in a wall of the chamber 286, and one or more attachment elements 288 for coupling the auto-focusing FRU 285 to the compact chassis assembly 201.

The auto-focusing FRU 285 can comprise one or more auto-focusing subsystems 190, and one or more controllers 194. For example, autofocus can be performed by scanning the measurement optics in the Z-direction and moving to the Z position that maximizes signal.

The auto-focusing FRU 285 can be coupled to the wafer-positioning FRU 290 using the optical connection devices (287 and 95) and one or more optical fibers 289. Alternatively, the auto-focusing FRU 285 can be coupled to the wafer-positioning FRU 290 using one or more optically transparent windows when the optical connection devices (287 and 95) include optically transparent windows. For example, the auto-focusing FRU 285 can be mounted next to and/or attached to the wafer-positioning chamber 291. Alternatively, other focusing techniques may be used.

When a failure occurs or when the performance degrades, one or more of the FRUs (205, 210, 215, 220, 225, 230, 235, 240, 245, 250, 255, 260, 265, 270, 275, 280, 285, and 290) can be replaced with a new unit. In some examples, a new FRU (205, 210, 215, 220, 225, 230, 235, 240, 245, 250, 255, 260, 265, 270, 275, 280, 285, and 290) can be obtained from a storage facility that can be located near-by, and the amount of down time can be minimized. In other examples, the failed FRU can be repaired and replaced in a short amount of time. When a new FRU is installed in the IMS 200, one or more of the other FRUs can be adjusted. In addition, when a new optical source is installed in the IMS 200, one or more of the FRUs (205, 210, 215, 220, 225, 230, 235, 240, 245, 250, 255, 260, 265, 270, 275, 280, 285, and 290) can be adjusted.

The attachment elements (208, 213, 218, 223, 228, 233, 238, 243, 248, 253, 258, 263, 268, 273, 278, 283, 288, and 293) can have thermal conductive properties, thermal isolation properties, mechanical properties, electrical properties, and/or vibration-reduction properties as required. For example, the attachment elements (208, 213, 218, 223, 228, 233, 238, 243, 248, 253, 258, 263, 268, 273, 278, 283, 288, and 293) can be configured to allow the FRUs (205, 210, 215, 220, 225, 230, 235, 240, 245, 250, 255, 260, 265, 270, 275, 280, 285, and 290) to be quickly and precisely coupled to and/or decoupled from the chamber wall and from one or more optical test benches (410, FIG. 4) used for testing and/or aligning. For example, when a FRU requires maintenance, it can be quickly and easily removed from the IMS 200 and can be tested using an optical test subsystem (400, FIG. 4).

One or more of the FRUs (205, 210, 215, 220, 225, 230, 235, 240, 245, 250, 255, 260, 265, 270, 275, 280, 285, and 290) can be used when performing real-time or non-real-time procedures. One or more of the controllers (107, 117, 124, 134, 137, 144, 147, 154, 157, 164, 167, 174, 177, 184, 187, 194, 195, and 197) can receive real-time or non-real-time data to update subsystem, processing element, process, recipe, profile, image, pattern, and/or model data. One or more of the controllers (107, 117, 124, 134, 137, 144, 147, 154, 157, 164, 167, 174, 177, 184, 187, 194, 195, and 197) can be coupled to one or more controllers 195 in a controller FRU 280 and can exchange data using one or more Semiconductor Equipment Communications Standard (SECS) messages, can read and/or remove information, can feed forward, and/or can feedback the information, and/or can send information as a SECS message.

Those skilled in the art will recognize that the controllers (107, 117, 124, 134, 137, 144, 147, 154, 157, 164, 167, 174, 177, 184, 187, 194, 195, and 197) can include hardware, firmware, and software (not shown) as required.

The controllers (107, 117, 124, 134, 137, 144, 147, 154, 157, 164, 167, 174, 177, 184, 187, 194, 195, and 197) can be used to control FRU operation when the FRU in installed in the IMS 200 or the optical test subsystem (400, FIG. 4).

In some examples, the controllers (107, 117, 124, 134, 137, 144, 147, 154, 157, 164, 167, 174, 177, 184, 187, 194, 195, and 197) can be used to turn-on or turn-off one or more components; can be used to turn-on or turn-off one or more of the optical beams; and can be used to determine the number of optical beams and one or more beam properties such as beam width and beam angle.

When two or more optical fibers are used, they must be matched and/or aligned properly, and the controllers (107, 117, 124, 134, 137, 144, 147, 154, 157, 164, 167, 174, 177, 184, 187, 194, 195, and 197) can be programmed to perform the aligning and/or matching procedures. In addition, when two or more optically transparent windows are used, they must be matched and/or aligned properly, the controllers (107, 117, 124, 134, 137, 144, 147, 154, 157, 164, 167, 174, 177, 184, 187, 194, 195, and 197) can be programmed to perform the aligning and/or matching procedures.

In still other configurations, some of the FRUs (205, 210, 215, 220, 225, 230, 235, 240, 245, 250, 255, 260, 265, 270, 275, 280, 285, and 290) can include some primary components to be used during operation and some secondary components that can be used to pre-align the FRU before installation. The secondary components can include positioning devices, light-collection optics, one or more shutters, and one or more filters. For example, the secondary components can be used to provide operational data. In addition, the inclusion of the secondary components in the FRUs can improve the reliability of the IMS 200 since the secondary components have a longer lifetime than the primary component of the system. For example, the primary components can have a more harmful working environment that can include high temperatures, constant motion, and exposure to DUV light. During a FRU maintenance procedure, the secondary components of the FRU can be inspected and re-conditioned under an off-line inspection and repair station for next maintenance. The reliability of the IMS 200 is improved significantly. Pre-aligning the key components in the FRU can also significantly reduce or eliminate the need of adjusting the other components or re-calibrating the system when the FRU is swapped.

In some embodiments, the IMS 200 can include Optical Digital Profilometry (ODP) elements (not shown), and ODP elements/systems are available from Timbre Technologies Inc. (a TEL company). Alternatively, other metrology data-extraction systems may be used.

The IMS 200 can use polarizing reflectometry, spectroscopic ellipsometry, spectroscopic reflectometry, or other optical measurement techniques to measure accurate device profiles, accurate CDs, and multiple layer film thickness of a wafer. The integrated metrology process (iODP) can be executed as an integrated process in an integrated group of subsystems. In addition, the integrated process eliminates the need to break the wafer for performing the analyses or waiting for long periods for data from external systems. iODP techniques can be used with the existing thin film metrology systems for inline profile and critical dimension (CD) measurement, and can be integrated with TEL processing systems and/or lithography systems to provide real-time process monitoring and control.

Data from the IMS 200 can include measured, predicted, and/or simulated data associated with the FRUs (205, 210, 215, 220, 225, 230, 235, 240, 245, 250, 255, 260, 265, 270, 275, 280, 285, and 290), and the data can be stored using processing, wafer, lot, recipe, site, or wafer location data. The data can include variables associated with the metrology devices, and metrology device models used in the various FRUs.

The IMS 200 can make measurements at two azimuth angles 180 degrees apart, and this technique can be used to reduce the sensitivity of the measurements to wafer tilt and other asymmetries in the optical system. The FRUs described herein can be used with other types of metrology systems.

Figure 3:
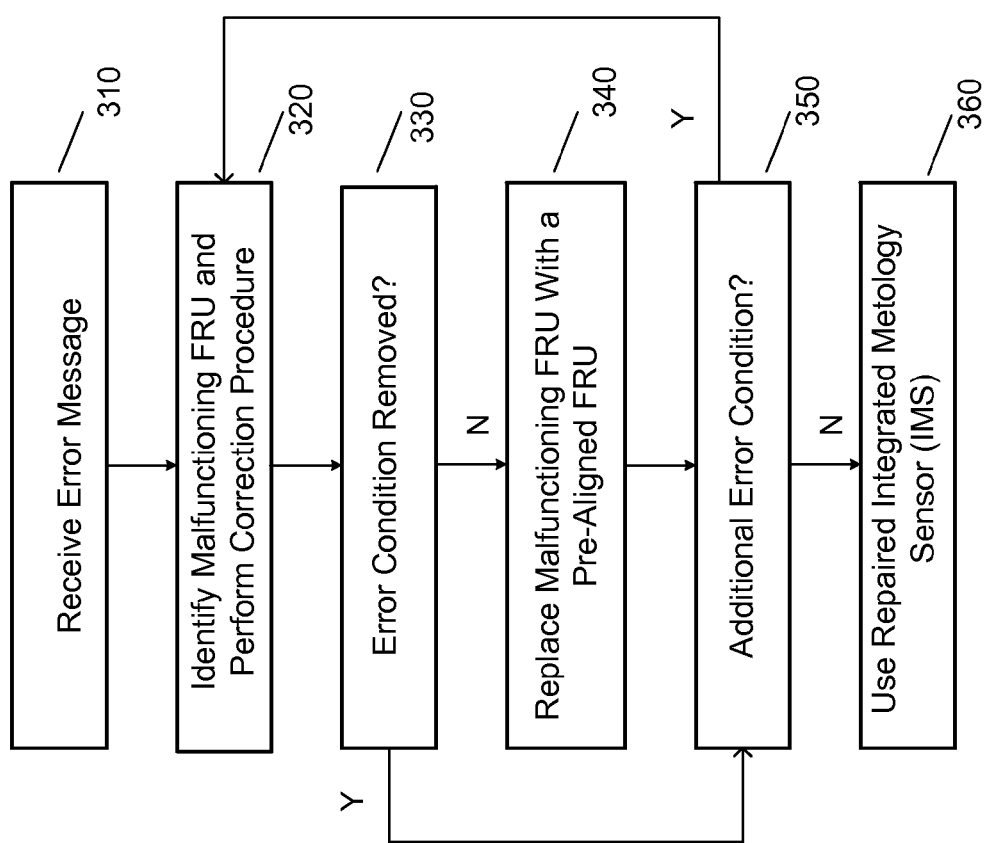
FIG. 3 illustrates an exemplary flow diagram of a procedure for using Field Replaceable Units (FRUs) in an optical Integrated Metrology Sensor (IMS) in accordance with embodiments of the invention.

FIG. 3 illustrates an exemplary flow diagram for a procedure for using an Integrated Metrology Sensor (IMS) in accordance with embodiments of the invention.

In 310, an error message can be received by a controller 195 in the IMS 200. Alternatively, the error message can be received by another controller. In some examples, the error message can identify a malfunctioning FRU. In other example, the IMS can detect an error condition by comparing an operating data to acceptable ranges and determining when the operating data (measurement) is outside the acceptable range.

In 320, a malfunctioning FRU can be identified, and a correction (repair) procedure can be established. In some examples, one or more tuning or alignment steps can be performed while the FRU is still installed in the IMS 200.

In 330, a query can be performed to determine if the identified error condition has been removed. When the identified error condition has been removed, procedure 300 can branch to step 350 and procedure 300 can continue as shown in FIG. 3. When the identified condition has not been removed, procedure 300 can branch to step 340 and procedure 300 can continue as shown in FIG. 3. the identified malfunctioning FRU can be replaced if the error condition cannot be eliminated.

In 340, the malfunctioning FRU can be replaced with a pre-aligned replacement FRU.

In 350, a query can be performed to determine if additional error conditions exist in the IMS. When additional error conditions exist, procedure 300 can branch to 320, and when the error conditions have been eliminated procedure 300 can branch to 360.

In 360, the repaired IMS can be used to measure wafers.

Figure 5:
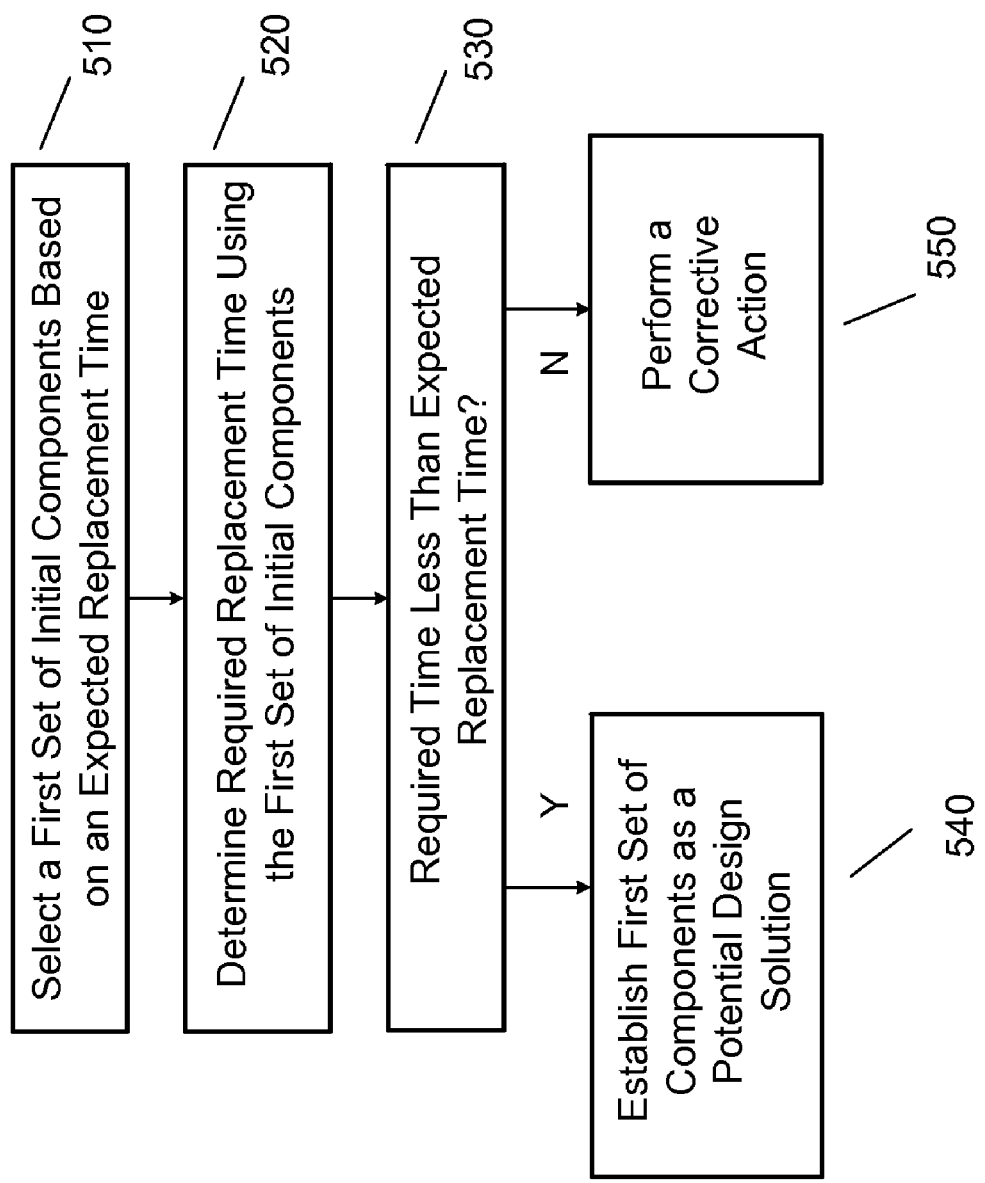
FIG. 5 illustrates an exemplary flow diagram of a procedure for creating a calibrated FRU for use in an Integrated Metrology Sensor (IMS) in accordance with embodiments of the invention.

FIG. 5 illustrates an exemplary flow diagram for a procedure for creating a calibrated FRU for use in an Integrated Metrology Sensor (IMS) in accordance with embodiments of the invention.

In 510, a first set of initial components can be selected based on an expected replacement time for the FRU when an FRU is initially designed.

In 520, a required replacement time can be determined. During the initial design procedures, the first set of initial components can be obtained, a FRU can be assembled, the FRU can be calibrated, the calibrated FRU can be installed, and the time required for these procedures can be established.

In 530, a query can be performed to determine if the determined required time is less than the expected replacement time for the FRU. When the required time is less than the replacement time, procedure 500 can branch to 540. When the required time is not less than the replacement time, procedure 500 can branch to 550.

In 540, the first set of initial components (initial design) can be established as a potential design solution.

In 550, one or more corrective actions can be performed. The corrective actions can include selecting a component from a different vendor, selecting a component with a faster assembly time, selecting a component with a faster calibration time, selecting a component with a shorter repair time, or selecting a component with a longer expected lifetime, or any combination thereof.

In some embodiments, operating an Integrated Metrology Sensor (IMS) can include: mounting a plurality of calibrated Field Replaceable Units (FRUs) using a plurality of pre-aligned mounting devices at pre-determined locations on the compact chassis assembly; positioning a wafer in a calibrated wafer-positioning FRU removably coupled to the compact chassis assembly and configured for supporting and aligning a wafer; providing one or more pre-aligned high-angle incident beams to a target on the wafer using a first set of calibrated FRUs, the first set of calibrated FRUs being removably coupled to the compact chassis assembly; receiving at least one pre-aligned high-angle diffracted beam from the target on the wafer using a second set of calibrated FRUs, the second set of calibrated FRUs being removably coupled to the compact chassis assembly; performing a first corrective action when a first error condition exists in one of the first set of calibrated FRUs, or in one of the second set of calibrated FRUs, or any combination thereof; and identifying the target using the at least one pre-aligned high-angle diffracted beam when the first error condition does not exist.

In addition, the first correction action can include tuning one or more of the calibrated FRUs, aligning one or more of the calibrated FRUs, repairing one or more of the calibrated FRUs, or replacing one or more of the calibrated FRUs with a pre-aligned replacement FRU, or any combination thereof.

In other embodiments, the operating method can further include: providing one or more pre-aligned low-angle incident beams to the target on the wafer using a third set of calibrated FRUs, the third set of calibrated FRUs being removably coupled to the compact chassis assembly; receiving at least one pre-aligned low-angle diffracted beam from the target on the wafer using a fourth set of calibrated FRUs, the fourth set of calibrated FRUs being removably coupled to the compact chassis assembly; performing a second corrective action when a second error condition exists in one of the third set of calibrated FRUs, or in one of the fourth set of calibrated FRUs, or any combination thereof; and identifying the target using the at least one pre-aligned low-angle diffracted beam when the second error condition does not exist.

FIG. 4 illustrates a simplified block diagram of a test subsystem in accordance with embodiments of the invention. In the illustrated embodiment, an optical test subsystem 400 is shown that includes an optical test bench 410, one or more optical test sources 420, one or more optical measurement tools, and a test controller 490. Alternately, other configurations may be used.

The test controller 490 can be coupled to the one or more optical test sources 420, to the FRU being tested, and to the one or more optical measurement tools. For example, the test controller can include test procedures for each of the FRUs (205, 210, 215, 220, 225, 230, 235, 240, 245, 250, 255, 260, 265, 270, 275, 280, 285, and 290). In some cases, one or more "golden" FRUs can be used to verify test and/or operational procedures.

In some examples, when alignment or testing is required, the second beam reflection FRU 245 can be aligned and/or tested in the IMS 200. In other examples, the second beam reflection FRU 245 can be easily removed from the IMS 200 and attached to the optical test bench (410, FIG. 4) in an optical test subsystem (400, FIG. 4) using attachment elements 243. During alignment or testing, one or more optical test sources (420, FIG. 4) can be coupled to one or more of the input optical connection devices 247a, and one or more measurement devices (430, FIG. 4) can be coupled to one or more of the output optical connection devices 247b. During alignment and/or testing, the characterization parameters of the second beam reflection FRU 245 can be tested and/or established using the optical test subsystem (400, FIG. 4). When the second beam reflection FRU 245 is being aligned and/or tested, one or more sets of characterization parameters can be used and/or updated.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

Thus, the description is not intended to limit the invention and the configuration, operation, and behavior of the present invention has been described with the understanding that modifications and variations of the embodiments are possible, given the level of detail present herein. Accordingly, the preceding detailed description is not mean or intended to, in any way, limit the invention—rather the scope of the invention is defined by the appended claims.

What is claimed:

1. A Integrated Metrology Sensor (IMS) comprising:
 a compact chassis assembly having a plurality of pre-aligned mounting devices configured for mounting a plurality of calibrated Field Replaceable Units (FRUs) at pre-determined locations, wherein the calibrated FRUs are assembled, aligned, and calibrated to meet a set characterization parameters;
 a calibrated wafer-positioning FRU removably coupled to the compact chassis assembly and configured for supporting and aligning a wafer;
 a calibrated high angle focusing FRU configured to provide one or more pre-aligned high-angle incident beams to a target on the wafer, the calibrated high angle focusing FRU being removably coupled to the calibrated wafer-positioning FRU and the compact chassis assembly;
 a calibrated high angle collecting FRU configured to receive one or more pre-aligned high-angle reflected beams from the target on the wafer, the calibrated high angle focusing FRU being removably coupled to the calibrated wafer-positioning FRU and the compact chassis assembly;
 a calibrated source FRU removably coupled to the compact chassis assembly and configured to provide at least one pre-aligned high angle input beam to the calibrated high angle focusing FRU; and
 a calibrated analyzer FRU removably coupled to the compact chassis assembly and configured to receive at least one pre-aligned high angle output beam.

2. The IMS as claimed in claim 1, further comprising:
 a calibrated low angle focusing FRU configured to provide one or more pre-aligned low-angle incident beams to the target on the wafer, the calibrated low angle focusing FRU being removably coupled to the calibrated wafer-positioning FRU and the compact chassis assembly, wherein the calibrated source FRU is further configured to provide at least one pre-aligned low angle input beam to the calibrated low angle focusing FRU; and
 a calibrated low angle collecting FRU configured to receive one or more pre-aligned low-angle diffracted beams from the target on the wafer, the calibrated low angle focusing FRU being removably coupled to the calibrated wafer-positioning FRU and the compact chassis assembly, wherein the calibrated analyzer FRU is further configured to receive at least one pre-aligned low angle output beam.

3. The IMS as claimed in claim 1, wherein the calibrated wafer-positioning FRU comprises a chamber, one or more optical connection devices mounted in a wall of the chamber, a controller, and one or more attachment elements configured for removably coupling the calibrated wafer-positioning FRU to the compact chassis assembly, each attachment element being configured to allow the calibrated wafer-positioning FRU to be quickly and precisely coupled to and/or decoupled from the compact chassis assembly.

4. The IMS as claimed in claim 3, wherein the calibrated wafer-positioning FRU further comprises a platform subsystem coupled to an interior wall of the chamber, a wafer-positioning subsystem coupled to the platform subsystem, and a wafer alignment sensor coupled to the wafer-positioning subsystem, wherein the calibrated wafer-positioning FRU is further configured to support, clamp, align, rotate, and/or translate the wafer.

5. The IMS as claimed in claim 4, wherein the calibrated wafer-positioning FRU further comprises a translation port for transferring the wafer into and/or out of the calibrated wafer-positioning FRU.

6. The IMS as claimed in claim 1, wherein the calibrated high angle focusing FRU comprises a chamber, one or more input optical connection devices mounted in a first wall of the chamber, one or more output optical windows mounted in a second wall of the chamber, a controller, and one or more attachment elements configured for removably coupling the calibrated high angle focusing FRU to the compact chassis assembly, each attachment element being configured to allow the calibrated high angle focusing FRU to be quickly and precisely coupled to and/or decoupled from the compact chassis assembly.

7. The IMS as claimed in claim 6, wherein the calibrated high angle focusing FRU further comprises one or more polarizers and a set of highly reflective curved surfaces configured for folding a light path and for correcting aberrations.

8. The IMS as claimed in claim 1, wherein the calibrated high angle collecting FRU comprises a chamber, one or more input optical windows mounted in a first wall of the chamber, one or more output optical connection devices mounted in a second wall of the chamber, a controller, and one or more attachment elements configured for removably coupling the calibrated high angle collecting FRU to the compact chassis assembly, each attachment element being configured to allow the calibrated high angle collecting FRU to be quickly and precisely coupled to and/or decoupled from the compact chassis assembly.

9. The IMS as claimed in claim 8, wherein the calibrated high angle collecting FRU further comprises one or more polarizers and a set of highly reflective curved surfaces configured for folding a light path and for correcting aberrations.

10. The IMS as claimed in claim 2, wherein the calibrated low angle focusing FRU comprises a chamber, one or more input optical connection devices mounted in a first wall of the chamber, one or more output optical windows mounted in a second wall of the chamber, a controller, and one or more attachment elements configured for removably coupling the calibrated low angle focusing FRU to the compact chassis assembly, each attachment element being configured to allow the calibrated low angle focusing FRU to be quickly and precisely coupled to and/or decoupled from the compact chassis assembly.

11. The IMS as claimed in claim 10, wherein the calibrated low angle focusing FRU further comprises one or more polarizers and a set of highly reflective curved surfaces configured for folding a light path and for correcting aberrations.

12. The IMS as claimed in claim 2, wherein the calibrated low angle collecting FRU comprises a chamber, one or more input optical windows mounted in a first wall of the chamber, one or more output optical connection devices mounted in a second wall of the chamber, a controller, and one or more attachment elements configured for removably coupling the calibrated low angle collecting FRU to the compact chassis assembly, each attachment element being configured to allow the calibrated low angle collecting FRU to be quickly and precisely coupled to and/or decoupled from the compact chassis assembly.

13. The IMS as claimed in claim 12, wherein the calibrated low angle collecting FRU further comprises one or more polarizers and a set of highly reflective curved surfaces configured for folding a light path and for correcting aberrations.

14. The IMS as claimed in claim 1, further comprising:
a first calibrated beam reflection FRU configured to provide a pre-aligned high angle input beam to the calibrated high angle focusing FRU, wherein the first calibrated beam reflection FRU is removably coupled to the calibrated high angle focusing FRU and the compact chassis assembly;
a first calibrated beam selector FRU removably coupled to the first calibrated beam reflection FRU and the compact chassis assembly;
a calibrated beam generator FRU removably coupled to the first calibrated beam selector FRU and the compact chassis assembly; and
a calibrated selector FRU removably coupled to the calibrated beam generator FRU and the compact chassis assembly, wherein the calibrated source FRU is coupled to the calibrated selector FRU.

15. The IMS as claimed in claim 1, further comprising;
a first calibrated beam selector FRU configured to provide a first calibrated input beam to a calibrated low angle focusing FRU, wherein the first calibrated input beam includes one or more calibrated low-angle incident beams, wherein the first calibrated beam selector FRU is removably coupled to the calibrated low angle focusing FRU and the compact chassis assembly;
a calibrated beam generator FRU removably coupled to the first calibrated beam selector FRU and the compact chassis assembly; and
a calibrated selector FRU removably coupled to the calibrated beam generator FRU and the compact chassis assembly, wherein the calibrated source FRU is coupled to the calibrated selector FRU.

16. The IMS as claimed in claim 1, further comprising;
a calibrated second beam reflection FRU configured to receive a calibrated first input beam from the calibrated high angle collecting FRU, wherein the calibrated first input beam includes one or more high-angle reflected beams wherein the calibrated second beam reflection FRU is removably coupled to the calibrated high angle collecting FRU and the compact chassis assembly; and
a calibrated second beam selector FRU removably coupled to the calibrated second beam reflection FRU and the compact chassis assembly, wherein the calibrated analyzer FRU is coupled to the calibrated second beam selector FRU.

17. The IMS as claimed in claim 1, further comprising;
a calibrated second beam selector FRU configured to receive a calibrated first input beam from a calibrated low angle collecting FRU, wherein the calibrated first input beam includes one or more calibrated low-angle reflected beams, the calibrated second beam selector FRU being removably coupled to the calibrated low angle collecting FRU and the compact chassis assembly, wherein the calibrated analyzer FRU is coupled to the calibrated second beam selector FRU.

* * * * *